US009662386B2

(12) United States Patent
Fujinaga et al.

(10) Patent No.: US 9,662,386 B2
(45) Date of Patent: May 30, 2017

(54) ADJUVANT FOR MUCOSAL VACCINE

(71) Applicant: OSAKA UNIVERSITY, Suita-shi, Osaka (JP)

(72) Inventors: Yukako Fujinaga, Osaka (JP); Takuhiro Matsumura, Osaka (JP); Masahiro Yutani, Osaka (JP); Nao Jonai, Tokyo (JP)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 15/223,566

(22) Filed: Jul. 29, 2016

(65) Prior Publication Data

US 2016/0324960 A1 Nov. 10, 2016

Related U.S. Application Data

(63) Continuation of application No. 14/649,279, filed as application No. PCT/JP2013/081459 on Nov. 15, 2013, now abandoned.

(30) Foreign Application Priority Data

Dec. 4, 2012 (JP) .................................. 2012-265532

(51) Int. Cl.
| | | |
|---|---|---|
| A61K 39/00 | (2006.01) | |
| A61K 39/12 | (2006.01) | |
| A61K 39/39 | (2006.01) | |
| A61K 39/02 | (2006.01) | |
| C07K 14/33 | (2006.01) | |
| A61K 39/145 | (2006.01) | |
| C07K 14/77 | (2006.01) | |
| C12N 7/00 | (2006.01) | |

(52) U.S. Cl.
CPC .............. *A61K 39/39* (2013.01); *A61K 39/00* (2013.01); *A61K 39/02* (2013.01); *A61K 39/12* (2013.01); *A61K 39/145* (2013.01); *C07K 14/33* (2013.01); *C07K 14/77* (2013.01); *C12N 7/00* (2013.01); *A61K 2039/5252* (2013.01); *A61K 2039/541* (2013.01); *A61K 2039/543* (2013.01); *A61K 2039/55516* (2013.01); *A61K 2039/55544* (2013.01); *A61K 2039/575* (2013.01); *C07K 2319/42* (2013.01); *C12N 2760/16134* (2013.01)

(58) Field of Classification Search
CPC ...................................................... A61K 39/39
See application file for complete search history.

(56) References Cited

U.S. PATENT DOCUMENTS

2007/0219149 A1    9/2007  Hasegawa et al.
2015/0306214 A1*  10/2015  Fujinaga ................ A61K 39/02
                                             424/197.11

FOREIGN PATENT DOCUMENTS

| JP | 2005-097267 A | 4/2005 |
|---|---|---|
| JP | 2009-081997 A | 4/2009 |
| JP | 2009-132686 A | 6/2009 |
| WO | WO 2005/070455 A1 | 8/2005 |

OTHER PUBLICATIONS

Supplementary European Search Report dated Jun. 6, 2016, in EP 13860873.2.
Kukreja et al., "Immunological characterization of the subunits of type A botulinum neurotoxin and different components of its associated proteins," Toxicon, May 1, 2009, 53(6):616-624.
International Search Report dated Jan. 28, 2014, in PCT/JP2013/081459.
Amatsu et al., "Crystal Structure of *Clostridium botulinum* Whole Hemagglutinin Reveals a Huge Triskelion-shaped Molecular Complex," The Journal of Biological Chemistry, Dec. 6, 2013, 288(49):35617-65325.
Fujinaga, Yukako, Report on Advanced Research Grant Implementation (Funding Program for Next Generation World-Leading Researchers) (Fiscal 2011), Research Project: Elucidation of invasion mechanisms of botulinum toxin complex in body and application of transmucosal vaccine delivery, Japan Society for the Promotion of Science, Nov. 16, 2012, with partial English translation.
Lee et al., "Production of anti-neurotoxin antibody is enhanced by two subcomponents, HA1 and HA3b, of *Clostridium botulinum* type B 16S toxin-haemagglutinin," Microbiology, 2005, 151:3739-3747.
Matsumura et al., "The botulinum toxin crosses the intestinal epithelial barrier via M cell," Japanese Journal of Bacteriology, 2009, 64(1):79.
Nakajima et al., "Molecular Composition of the 16S Toxin Produced by *Clostridium botulinum* Type D Strain, 1873," Microbiol Immunol., 1998, 42(9):599-605.
Takahashi et al., "Mechanisms for Mucosal Immunogenicity and Adjuvancy of *Eschericia coli* Labile Enterotoxin," The Journal of Infectious Diseases, 1996, 173:627-635.
Xu-Amano et al., "Helper-T Cell Subsets for Immunoglobulin A Responses: Oral Immunization with Tetanus Toxoid and Cholera Toxin as Adjuvant Selectively Induces Th2 Cells in Mucosa Associated Tissues," J. Exp. Med., Oct. 1993, 178:1309-1320.
Amatsu et al., "Crystal Structure of *Clostridium botulinum* Whole Hemagglutinin Reveals a Huge Triskelion-shaped Molecular Complex," The Journal of Biological Chemistry, Dec. 6, 2013, 288(49):35617-35625.

(Continued)

*Primary Examiner* — Albert Navarro
(74) *Attorney, Agent, or Firm* — Foley & Lardner LLP

(57) ABSTRACT

An object of the present invention is to provide an adjuvant for a mucosal vaccine with high safety that induces a sufficient immune response on the mucosa. According to the present invention, an adjuvant for a mucosal vaccine comprising a protein complex composed of hemagglutinin (HA) subcomponents HA1, HA2, and HA3 of *botulinum* toxin is provided.

9 Claims, 10 Drawing Sheets

(56) References Cited

OTHER PUBLICATIONS

Fujinaga, Yukako, "Elucidation of the mechanism of the botulinum toxin complex for promoting intestinal absorption and development of a novel drug delivery system based on the mechanism," Research Papers of the Suzuken Memorial Foundation, Feb. 2011, 28:298-301, with partial English translation of indicated portions.

Kunisawa et al., "Drug delivery systems for the development of prospective mucosal vaccine," Drug Delivery System, 2008, 23(2):116-122, with English summary on first page reproduced for clarity.

Matsumura et al., "Type A HA-positive botulinum toxin complex crosses the intestinal epithelial barrier via M cell," Toxins 2012, Miami Beach, FL, USA, Dec. 5-8, 2012, posters, p. 101.

Sato et al., "New trends in vaccine development for the prevention of mucosal infections," Experimental Medicine, Chapter 6: Use of dendritic cells for clinical applications, 2008, 28(20 extra issue):3340-3346, with English abstract.

Sugawara et al., "Botulinum hemagglutinin disrupts the intercellular epithelial barrier by directly binding E-cadherin," J. Cell. Biol., May 10, 2010, 189(4):691-700.

Suzuki et al., "The Development of Mucosal Vaccine Using Bacterial Function for Targeting Mucosal Tissues," Journal of the Pharmaceutical Society of Japan, May 2014, 134(5):629-634, with English summary on first page.

Takegahara et al., "Analysis of activity of subunits constituting the botulinum HA complex for destroying the intercellular barrier of intestinal epithelial cells," Japanese Journal of Bacteriology, 2008, 63(1):111, 1-H-8/P111, with English translation.

\* cited by examiner

Fig. 1

FLAG-BHA1
MDYKDDDDKLIQNSLNDKIVTISCKANTDLFFYQVPGNGNVSLFQQTRNYLERWRIIYDSNKAAYKIKSMNIYNTNLV
LTWNAPTHNISAQQDSNADNQYWLLLKDIGNNSFIIASYKNPNLVLYADTVARNLKLSTLNNSSYIKFIIEDYVISDF
KNFTCRISPILAGGKVVQQVSMTNLAVNLYIWNNDLNQKWTITYNEEKAAYQFFNKILSNGVLTWIFSDGNTVRVSSS
AQNNDAQYWLINPVSDNYDRYTITNLRDKTKVLDLYGGQTADGTTIQVFNSNGGDNQIWTMSNP

FLAG-BHA2
MDYKDDDDKLSAERTFLPNGNYNIKSIFSGSLYLSPVSGSLTFSNESSANNQKWNVEYMAENRCFKISNVAEPNKYLS
YDNFGFISLDSLSNRCYWFPIKIAVNTYIMLSLNKVNELDYAWDIYDTNENILSQPLLLLPNFDIYNSNQMFKLEKI

Strep-BHA3
MASWSHPQFEKGALEVLFQGPGYQYSDTIDLADGNYVVSRGDGWILSRQNQILGGSVISNGSTGIVGDLRVNDNAIPY
YYPTPSFNEEYIKNNIQTVFANFTEANQIPIGFEFSKTAPSNKNLYMYLQYTYIRYEIIKVLQHEIIERAVLYVPSLG
YVKSIEFNPGEKINKDFYFLTNDKCILNEQFLYKKILETTKNIPTNNIFNSKVSSTQRVLPYSNGLYVINKGDGYIRT
NDKDLIGTLLIEAGSSGSIIQPRLRNTTRPLFTTSNDAKFSQQYTEERLKDAFNVQLFNTSTSLFKPVEEAPSNKNIC
IKAYNTYEKYELIDYQNGSIVNKAEYYLPSLGYCEVTNAPSPESEVVKTQVAEDGFIQNGPEEEIVVGVIDPSENIQE
INTAISDNYTYNIPGIVNNNPFYILFTVNTTGIYKINAQNNLPSLKIYEAIGSGNRNPQSGNLCDDDIKAINYITGFD
SPNAKSYLVVLLNKDKNYYIRVPQTSSNIENQIKFKREEGDLRNLMNSSVNIIDNLNSTGAHYYTRQSPDVHDYISYE
FTIPGNFNNKDTSNIRLYTSYNQGIGTLFRVTETIDGYNLINIQQNLNLLNSTKSIRLLNGAIYILKVEVTELNNYNI
KLHIDITN Elution (ml)

SEQUENCE LISTING

```
<160> NUMBER OF SEQ ID NOS: 14

<210> SEQ ID NO 1
<211> LENGTH: 294
<212> TYPE: PRT
<213> ORGANISM: Clostridium botulinum

<400> SEQUENCE: 1

Met Glu His Tyr Ser Thr Ile Gln Asn Ser Leu Asn Asp Lys Ile Val
1               5                   10                  15

Thr Ile Ser Cys Lys Ala Asn Thr Asp Leu Phe Phe Tyr Gln Val Pro
                20                  25                  30

Gly Asn Gly Asn Val Ser Leu Phe Gln Gln Thr Arg Asn Tyr Leu Glu
            35                  40                  45

Arg Trp Arg Ile Ile Tyr Asp Ser Asn Lys Ala Ala Tyr Lys Ile Lys
        50                  55                  60

Ser Met Asn Ile Tyr Asn Thr Asn Leu Val Leu Thr Trp Asn Ala Pro
65                  70                  75                  80

Thr His Asn Ile Ser Ala Gln Gln Asp Ser Asn Ala Asp Asn Gln Tyr
                85                  90                  95

Trp Leu Leu Leu Lys Asp Ile Gly Asn Asn Ser Phe Ile Ile Ala Ser
            100                 105                 110

Tyr Lys Asn Pro Asn Leu Val Leu Tyr Ala Asp Thr Val Ala Arg Asn
        115                 120                 125

Leu Lys Leu Ser Thr Leu Asn Asn Ser Ser Tyr Ile Lys Phe Ile Ile
    130                 135                 140

Glu Asp Tyr Val Ile Ser Asp Phe Lys Asn Phe Thr Cys Arg Ile Ser
145                 150                 155                 160

Pro Ile Leu Ala Gly Gly Lys Val Val Gln Gln Val Ser Met Thr Asn
                165                 170                 175

Leu Ala Val Asn Leu Tyr Ile Trp Asn Asn Asp Leu Asn Gln Lys Trp
            180                 185                 190

Thr Ile Ile Tyr Asn Glu Glu Lys Ala Ala Tyr Gln Phe Phe Asn Lys
        195                 200                 205

Ile Leu Ser Asn Gly Val Leu Thr Trp Ile Phe Ser Asp Gly Asn Thr
    210                 215                 220

Val Arg Val Ser Ser Ala Gln Asn Asn Asp Ala Gln Tyr Trp Leu
225                 230                 235                 240

Ile Asn Pro Val Ser Asp Asn Tyr Asp Arg Tyr Thr Ile Thr Asn Leu
                245                 250                 255

Arg Asp Lys Thr Lys Val Leu Asp Leu Tyr Gly Gly Gln Thr Ala Asp
            260                 265                 270

Gly Thr Thr Ile Gln Val Phe Asn Ser Asn Gly Gly Asp Asn Gln Ile
        275                 280                 285

Trp Thr Met Ser Asn Pro
    290
```

```
<210> SEQ ID NO 2
<211> LENGTH: 146
<212> TYPE: PRT
<213> ORGANISM: Clostridium botulinum

<400> SEQUENCE: 2

Met Ser Ala Glu Arg Thr Phe Leu Pro Asn Gly Asn Tyr Asn Ile Lys
1               5                   10                  15

Ser Ile Phe Ser Gly Ser Leu Tyr Leu Ser Pro Val Ser Gly Ser Leu
            20                  25                  30

Thr Phe Ser Asn Glu Ser Ser Ala Asn Asn Gln Lys Trp Asn Val Glu
        35                  40                  45

Tyr Met Ala Glu Asn Arg Cys Phe Lys Ile Ser Asn Val Ala Glu Pro
50                  55                  60

Asn Lys Tyr Leu Ser Tyr Asp Asn Phe Gly Phe Ile Ser Leu Asp Ser
65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
            100                 105                 110

Asp Ile Tyr Asp Thr Asn Glu Asn Ile Leu Ser Gln Pro Leu Leu Leu
        115                 120                 125

Leu Pro Asn Phe Asp Ile Tyr Asn Ser Asn Gln Met Phe Lys Leu Glu
130                 135                 140

Lys Ile
145

<210> SEQ ID NO 3
<211> LENGTH: 626
<212> TYPE: PRT
<213> ORGANISM: Clostridium botulinum

<400> SEQUENCE: 3

Met Asn Ser Ser Ile Lys Lys Ile Tyr Asn His Ile Gln Glu Lys Val
1               5                   10                  15

Ile Asn Tyr Ser Asp Thr Ile Asp Leu Ala Asp Gly Asn Tyr Val Val
            20                  25                  30

Ser Arg Gly Asp Gly Trp Ile Leu Ser Arg Gln Asn Gln Ile Leu Gly
        35                  40                  45

Gly Ser Val Ile Ser Asn Gly Ser Thr Gly Ile Val Gly Asp Leu Arg
50                  55                  60

Val Asn Asp Asn Ala Ile Pro Tyr Tyr Tyr Pro Thr Pro Ser Phe Asn
65                  70                  75                  80

Glu Glu Tyr Ile Lys Asn Asn Ile Gln Thr Val Phe Ala Asn Phe Thr
                85                  90                  95

Glu Ala Asn Gln Ile Pro Ile Gly Phe Glu Phe Ser Lys Thr Ala Pro
            100                 105                 110

Ser Asn Lys Asn Leu Tyr Met Tyr Leu Gln Tyr Thr Tyr Ile Arg Tyr
        115                 120                 125

Glu Ile Ile Lys Val Leu Gln His Glu Ile Ile Glu Arg Ala Val Leu
130                 135                 140

Tyr Val Pro Ser Leu Gly Tyr Val Lys Ser Ile Glu Phe Asn Pro Gly
145                 150                 155                 160

Glu Lys Ile Asn Lys Asp Phe Tyr Phe Leu Thr Asn Asp Lys Cys Ile
                165                 170                 175
```

-continued

Leu Asn Glu Gln Phe Leu Tyr Lys Lys Ile Leu Glu Thr Thr Lys Asn
                180                 185                 190

Ile Pro Thr Asn Asn Ile Phe Asn Ser Lys Val Ser Ser Thr Gln Arg
            195                 200                 205

Val Leu Pro Tyr Ser Asn Gly Leu Tyr Val Ile Asn Lys Gly Asp Gly
210                 215                 220

Tyr Ile Arg Thr Asn Asp Lys Asp Leu Ile Gly Thr Leu Leu Ile Glu
225                 230                 235                 240

Ala Gly Ser Ser Gly Ser Ile Ile Gln Pro Arg Leu Arg Asn Thr Thr
                245                 250                 255

Arg Pro Leu Phe Thr Thr Ser Asn Asp Ala Lys Phe Ser Gln Gln Tyr
            260                 265                 270

Thr Glu Glu Arg Leu Lys Asp Ala Phe Asn Val Gln Leu Phe Asn Thr
        275                 280                 285

Ser Thr Ser Leu Phe Lys Phe Val Glu Glu Ala Pro Ser Asn Lys Asn
    290                 295                 300

Ile Cys Ile Lys Ala Tyr Asn Thr Tyr Glu Lys Tyr Glu Leu Ile Asp
305                 310                 315                 320

Tyr Gln Asn Gly Ser Ile Val Asn Lys Ala Glu Tyr Tyr Leu Pro Ser
                325                 330                 335

Leu Gly Tyr Cys Glu Val Thr Asn Ala Pro Ser Pro Glu Ser Glu Val
            340                 345                 350

Val Lys Thr Gln Val Ala Glu Asp Gly Phe Ile Gln Asn Gly Pro Glu
        355                 360                 365

Glu Glu Ile Val Val Gly Val Ile Asp Pro Ser Glu Asn Ile Gln Glu
    370                 375                 380

Ile Asn Thr Ala Ile Ser Asp Asn Tyr Thr Tyr Asn Ile Pro Gly Ile
385                 390                 395                 400

Val Asn Asn Asn Pro Phe Tyr Ile Leu Phe Thr Val Asn Thr Thr Gly
                405                 410                 415

Ile Tyr Lys Ile Asn Ala Gln Asn Asn Leu Pro Ser Leu Lys Ile Tyr
            420                 425                 430

Glu Ala Ile Gly Ser Gly Asn Arg Asn Phe Gln Ser Gly Asn Leu Cys
        435                 440                 445

Asp Asp Asp Ile Lys Ala Ile Asn Tyr Ile Thr Gly Phe Asp Ser Pro
    450                 455                 460

Asn Ala Lys Ser Tyr Leu Val Val Leu Leu Asn Lys Asp Lys Asn Tyr
465                 470                 475                 480

Tyr Ile Arg Val Pro Gln Thr Ser Ser Asn Ile Glu Asn Gln Ile Lys
                485                 490                 495

Phe Lys Arg Glu Glu Gly Asp Leu Arg Asn Leu Met Asn Ser Ser Val
            500                 505                 510

Asn Ile Ile Asp Asn Leu Asn Ser Thr Gly Ala His Tyr Tyr Thr Arg
        515                 520                 525

Gln Ser Pro Asp Val His Asp Tyr Ile Ser Tyr Glu Phe Thr Ile Pro
    530                 535                 540

Gly Asn Phe Asn Asn Lys Asp Thr Ser Asn Ile Arg Leu Tyr Thr Ser
545                 550                 555                 560

Tyr Asn Gln Gly Ile Gly Thr Leu Phe Arg Val Thr Glu Thr Ile Asp
                565                 570                 575

Gly Tyr Asn Leu Ile Asn Ile Gln Gln Asn Leu Asn Leu Leu Asn Ser
            580                 585                 590

```
Thr Lys Ser Ile Arg Leu Leu Asn Gly Ala Ile Tyr Ile Leu Lys Val
        595                 600                 605

Glu Val Thr Glu Leu Asn Asn Tyr Asn Ile Lys Leu His Ile Asp Ile
    610                 615                 620

Thr Asn
625

<210> SEQ ID NO 4
<211> LENGTH: 885
<212> TYPE: DNA
<213> ORGANISM: Clostridium botulinum
<220> FEATURE:
<221> NAME/KEY: CDS
<222> LOCATION: (1)..(885)

<400> SEQUENCE: 4 atg gaa cac tat tca aca atc caa aat tca tta aat gac aaa atc gtt      48
Met Glu His Tyr Ser Thr Ile Gln Asn Ser Leu Asn Asp Lys Ile Val
1               5                   10                  15 acc atc tcc tgt aag gct aat aca gat tta ttt ttt tat caa gtt ccc      96
Thr Ile Ser Cys Lys Ala Asn Thr Asp Leu Phe Phe Tyr Gln Val Pro
            20                  25                  30 ggt aac ggt aac gtt agc tta ttt caa caa act aga aat tac ctt gaa     144
Gly Asn Gly Asn Val Ser Leu Phe Gln Gln Thr Arg Asn Tyr Leu Glu
        35                  40                  45 aga tgg aga att ata tat gat tct aat aaa gct gct tat aaa ata aaa     192
Arg Trp Arg Ile Ile Tyr Asp Ser Asn Lys Ala Ala Tyr Lys Ile Lys
    50                  55                  60 agt atg aat atc tat aat act aat tta gtt tta aca tgg aat gca cca     240
Ser Met Asn Ile Tyr Asn Thr Asn Leu Val Leu Thr Trp Asn Ala Pro
65                  70                  75                  80 aca cat aat ata tca gcg caa caa gat tca aat gca gat aat caa tat     288
Thr His Asn Ile Ser Ala Gln Gln Asp Ser Asn Ala Asp Asn Gln Tyr
                85                  90                  95 tgg tta tta tta aaa gac att ggt aac aat tca ttt att att gca agt     336
Trp Leu Leu Leu Lys Asp Ile Gly Asn Asn Ser Phe Ile Ile Ala Ser
            100                 105                 110 tat aaa aac cct aac tta gta tta tat gct gat acc gta gct cgt aat     384
Tyr Lys Asn Pro Asn Leu Val Leu Tyr Ala Asp Thr Val Ala Arg Asn
        115                 120                 125 ttg aag ctt agc aca ctt aat aat tca agt tat ata aaa ttt atc ata     432
Leu Lys Leu Ser Thr Leu Asn Asn Ser Ser Tyr Ile Lys Phe Ile Ile
    130                 135                 140 gaa gat tat gta ata tca gat ttt aaa aat ttc aca tgt aga ata agt     480
Glu Asp Tyr Val Ile Ser Asp Phe Lys Asn Phe Thr Cys Arg Ile Ser
145                 150                 155                 160 cca ata tta gcc ggt ggt aaa gtt gta caa caa gtg tct atg aca aat     528
Pro Ile Leu Ala Gly Gly Lys Val Val Gln Gln Val Ser Met Thr Asn
                165                 170                 175 cta gct gtt aat tta tat att tgg aac aat gat ctc aat caa aaa tgg     576
Leu Ala Val Asn Leu Tyr Ile Trp Asn Asn Asp Leu Asn Gln Lys Trp
            180                 185                 190 aca att ata tat aat gaa gaa aaa gca gca tac cag ttt ttt aat aaa     624
Thr Ile Ile Tyr Asn Glu Glu Lys Ala Ala Tyr Gln Phe Phe Asn Lys
        195                 200                 205 ata ctt tca aac gga gtt cta aca tgg att ttt tca gat ggt aat act     672
Ile Leu Ser Asn Gly Val Leu Thr Trp Ile Phe Ser Asp Gly Asn Thr
    210                 215                 220 gta aga gtt tct tct agt gcg caa aac aat gat gcc caa tat tgg ctt     720
Val Arg Val Ser Ser Ser Ala Gln Asn Asn Asp Ala Gln Tyr Trp Leu
225                 230                 235                 240
```

```
ata aat cct gtt tca gat aat tat gac aga tat aca att act aat cta      768
Ile Asn Pro Val Ser Asp Asn Tyr Asp Arg Tyr Thr Ile Thr Asn Leu
            245                 250                 255 cgc gat aaa act aaa gtt cta gat tta tat ggc ggc caa aca gca gac      816
Arg Asp Lys Thr Lys Val Leu Asp Leu Tyr Gly Gly Gln Thr Ala Asp
        260                 265                 270 gga act act att caa gta ttt aat tct aat gga ggt gat aat cag ata      864
Gly Thr Thr Ile Gln Val Phe Asn Ser Asn Gly Gly Asp Asn Gln Ile
            275                 280                 285 tgg act atg agt aac cca taa                                          885
Trp Thr Met Ser Asn Pro
    290
```

<210> SEQ ID NO 5
<211> LENGTH: 441
<212> TYPE: DNA
<213> ORGANISM: Clostridium botulinum
<220> FEATURE:
<221> NAME/KEY: CDS
<222> LOCATION: (1)..(441)

<400> SEQUENCE: 5

```
atg tca gct gaa aga act ttt cta cct aat ggt aat tac aat ata aaa       48
Met Ser Ala Glu Arg Thr Phe Leu Pro Asn Gly Asn Tyr Asn Ile Lys
1               5                   10                  15 tct atc ttt tct ggt tct tta tat tta agt cct gta tca gga tca tta       96
Ser Ile Phe Ser Gly Ser Leu Tyr Leu Ser Pro Val Ser Gly Ser Leu
            20                  25                  30 aca ttt tca aat gaa tct tct gca aat aat caa aaa tgg aat gta gaa      144
Thr Phe Ser Asn Glu Ser Ser Ala Asn Asn Gln Lys Trp Asn Val Glu
        35                  40                  45 tat atg gct gaa aat aga tgc ttt aaa atc tct aat gta gca gaa cca      192
Tyr Met Ala Glu Asn Arg Cys Phe Lys Ile Ser Asn Val Ala Glu Pro
    50                  55                  60 aat aag tat tta agt tac gat aac ttt gga ttt att tct tta gat tca      240
Asn Lys Tyr Leu Ser Tyr Asp Asn Phe Gly Phe Ile Ser Leu Asp Ser
65                  70                  75                  80 tta tct aat aga tgc tac tgg ttt cct att aaa atc gct gta aat act      288
Leu Ser Asn Arg Cys Tyr Trp Phe Pro Ile Lys Ile Ala Val Asn Thr
                85                  90                  95 tat att atg tta agt tta aat aaa gtg aat gaa tta gat tat gcc tgg      336
Tyr Ile Met Leu Ser Leu Asn Lys Val Asn Glu Leu Asp Tyr Ala Trp
            100                 105                 110 gac att tat gat act aat gaa aat att tta agt cag cca cta ctc cta      384
Asp Ile Tyr Asp Thr Asn Glu Asn Ile Leu Ser Gln Pro Leu Leu Leu
        115                 120                 125 cta cct aat ttt gat ata tac aat tca aat caa atg ttc aaa ctt gaa      432
Leu Pro Asn Phe Asp Ile Tyr Asn Ser Asn Gln Met Phe Lys Leu Glu
    130                 135                 140 aaa ata taa                                                          441
Lys Ile
145
```

<210> SEQ ID NO 6
<211> LENGTH: 1881
<212> TYPE: DNA
<213> ORGANISM: Clostridium botulinum
<220> FEATURE:
<221> NAME/KEY: CDS
<222> LOCATION: (1)..(1881)

<400> SEQUENCE: 6

```
atg aat tca tct ata aaa aaa att tat aat cat ata caa gaa aaa gtt      48
Met Asn Ser Ser Ile Lys Lys Ile Tyr Asn His Ile Gln Glu Lys Val
1               5                   10                  15 ata aac tat agt gat act att gat tta gct gat ggt aat tat gta gtt      96
Ile Asn Tyr Ser Asp Thr Ile Asp Leu Ala Asp Gly Asn Tyr Val Val
            20                  25                  30 agc aga ggg gat gga tgg ata tta tct aga caa aat caa ata cta ggt     144
Ser Arg Gly Asp Gly Trp Ile Leu Ser Arg Gln Asn Gln Ile Leu Gly
        35                  40                  45 gga agt gta att agt aat gga tca aca gga ata gtt ggg gac cta cgt     192
Gly Ser Val Ile Ser Asn Gly Ser Thr Gly Ile Val Gly Asp Leu Arg
    50                  55                  60 gta aat gat aat gcg ata cca tat tat tat cca aca cca tcc ttc aat     240
Val Asn Asp Asn Ala Ile Pro Tyr Tyr Tyr Pro Thr Pro Ser Phe Asn
65                  70                  75                  80 gaa gaa tat ata aaa aat aat ata caa act gta ttt gct aac ttt act     288
Glu Glu Tyr Ile Lys Asn Asn Ile Gln Thr Val Phe Ala Asn Phe Thr
                85                  90                  95 gaa gct aat caa att cca ata gga ttt gaa ttt agt aaa acc gct ccc     336
Glu Ala Asn Gln Ile Pro Ile Gly Phe Glu Phe Ser Lys Thr Ala Pro
            100                 105                 110 tca aat aaa aac tta tat atg tat tta caa tat acc tac att aga tat     384
Ser Asn Lys Asn Leu Tyr Met Tyr Leu Gln Tyr Thr Tyr Ile Arg Tyr
        115                 120                 125 gaa ata ata aaa gtc ttg caa cat gaa att ata gaa aga gca gtt tta     432
Glu Ile Ile Lys Val Leu Gln His Glu Ile Ile Glu Arg Ala Val Leu
    130                 135                 140 tat gtt cca tct ctt gga tat gtt aag tct ata gaa ttt aat cca ggg     480
Tyr Val Pro Ser Leu Gly Tyr Val Lys Ser Ile Glu Phe Asn Pro Gly
145                 150                 155                 160 gaa aaa ata aat aaa gat ttt tac ttt tta act aat gat aag tgc att     528
Glu Lys Ile Asn Lys Asp Phe Tyr Phe Leu Thr Asn Asp Lys Cys Ile
                165                 170                 175 tta aat gaa caa ttc cta tat aaa aaa att tta gaa act act aaa aat     576
Leu Asn Glu Gln Phe Leu Tyr Lys Lys Ile Leu Glu Thr Thr Lys Asn
            180                 185                 190 ata cca act aac aat att ttt aat tct aaa gtt agt agc aca caa cga     624
Ile Pro Thr Asn Asn Ile Phe Asn Ser Lys Val Ser Ser Thr Gln Arg
        195                 200                 205 gta ttg cct tat agt aat gga cta tat gtt att aat aag ggt gat gga     672
Val Leu Pro Tyr Ser Asn Gly Leu Tyr Val Ile Asn Lys Gly Asp Gly
    210                 215                 220 tat ata aga aca aat gat aaa gat ttg ata ggt aca tta tta atc gaa     720
Tyr Ile Arg Thr Asn Asp Lys Asp Leu Ile Gly Thr Leu Leu Ile Glu
225                 230                 235                 240 gca ggt tca tca gga agt att ata caa cct cga tta aga aat aca act     768
Ala Gly Ser Ser Gly Ser Ile Ile Gln Pro Arg Leu Arg Asn Thr Thr
                245                 250                 255 agg cca tta ttc acc aca agt aat gat gca aaa ttc tca caa caa tat     816
Arg Pro Leu Phe Thr Thr Ser Asn Asp Ala Lys Phe Ser Gln Gln Tyr
            260                 265                 270 act gaa gaa aga ctt aaa gac gct ttc aat gta caa tta ttt aat aca     864
Thr Glu Glu Arg Leu Lys Asp Ala Phe Asn Val Gln Leu Phe Asn Thr
        275                 280                 285 tca aca tcg tta ttt aaa ttt gta gaa gaa gct cct tca aat aaa aat     912
Ser Thr Ser Leu Phe Lys Phe Val Glu Glu Ala Pro Ser Asn Lys Asn
    290                 295                 300 ata tgc ata aag gct tat aat acc tat gaa aag tat gaa tta ata gac     960
Ile Cys Ile Lys Ala Tyr Asn Thr Tyr Glu Lys Tyr Glu Leu Ile Asp
305                 310                 315                 320
```

```
tat caa aat gga agt att gtt aat aaa gct gag tat tac ctt cct tcc      1008
Tyr Gln Asn Gly Ser Ile Val Asn Lys Ala Glu Tyr Tyr Leu Pro Ser
                325             330             335 tta gga tat tgt gaa gta act aat gct cct tca cct gaa tct gaa gta      1056
Leu Gly Tyr Cys Glu Val Thr Asn Ala Pro Ser Pro Glu Ser Glu Val
            340             345             350 gtt aaa acg caa gtg gct gaa gat gga ttt ata cag aat ggc ccc gag      1104
Val Lys Thr Gln Val Ala Glu Asp Gly Phe Ile Gln Asn Gly Pro Glu
        355             360             365 gaa gaa atc gta gta ggt gtc ata gac cca tct gaa aat ata caa gaa      1152
Glu Glu Ile Val Val Gly Val Ile Asp Pro Ser Glu Asn Ile Gln Glu
    370             375             380 ata aat act gct att tca gat aat tac aca tat aac att ccg ggt att      1200
Ile Asn Thr Ala Ile Ser Asp Asn Tyr Thr Tyr Asn Ile Pro Gly Ile
385             390             395             400 gta aat aat aat cca ttt tat ata tta ttt aca gta aat act aca gga      1248
Val Asn Asn Asn Pro Phe Tyr Ile Leu Phe Thr Val Asn Thr Thr Gly
                405             410             415 att tat aaa att aat gct caa aat aat cta cca tca tta aaa ata tat      1296
Ile Tyr Lys Ile Asn Ala Gln Asn Asn Leu Pro Ser Leu Lys Ile Tyr
            420             425             430 gaa gcg ata ggt tct ggt aat aga aat ttc caa tct ggg aat tta tgt      1344
Glu Ala Ile Gly Ser Gly Asn Arg Asn Phe Gln Ser Gly Asn Leu Cys
        435             440             445 gat gat gat att aaa gca ata aat tat att act ggg ttt gac agt cct      1392
Asp Asp Asp Ile Lys Ala Ile Asn Tyr Ile Thr Gly Phe Asp Ser Pro
    450             455             460 aat gct aaa agt tat tta gtt gtt ttg ctt aat aag gat aaa aat tac      1440
Asn Ala Lys Ser Tyr Leu Val Val Leu Leu Asn Lys Asp Lys Asn Tyr
465             470             475             480 tac att aga gta cca caa act tct tct aat ata gaa aat caa ata aaa      1488
Tyr Ile Arg Val Pro Gln Thr Ser Ser Asn Ile Glu Asn Gln Ile Lys
                485             490             495 ttc aag aga gaa gaa ggg gat ctc cga aat tta atg aat tct tca gtt      1536
Phe Lys Arg Glu Glu Gly Asp Leu Arg Asn Leu Met Asn Ser Ser Val
            500             505             510 aat ata ata gat aat ctt aat tca aca ggt gca cat tac tat aca aga      1584
Asn Ile Ile Asp Asn Leu Asn Ser Thr Gly Ala His Tyr Tyr Thr Arg
        515             520             525 caa agc cct gat gtc cat gac tat att tca tat gaa ttt aca ata cct      1632
Gln Ser Pro Asp Val His Asp Tyr Ile Ser Tyr Glu Phe Thr Ile Pro
    530             535             540 ggt aac ttt aat aat aaa gat aca tct aac att agg ctt tat act agt      1680
Gly Asn Phe Asn Asn Lys Asp Thr Ser Asn Ile Arg Leu Tyr Thr Ser
545             550             555             560 tat aac caa gga ata ggt act tta ttt aga gtc act gaa act att gac      1728
Tyr Asn Gln Gly Ile Gly Thr Leu Phe Arg Val Thr Glu Thr Ile Asp
                565             570             575 ggc tat aat tta att aat ata caa caa aat tta aat ctc tta aat agt      1776
Gly Tyr Asn Leu Ile Asn Ile Gln Gln Asn Leu Asn Leu Leu Asn Ser
            580             585             590 acc aag tca ata cgt tta tta aat ggt gca att tat ata tta aaa gta      1824
Thr Lys Ser Ile Arg Leu Leu Asn Gly Ala Ile Tyr Ile Leu Lys Val
        595             600             605 gaa gtt aca gaa tta aat aac tat aat ata aaa ttg cat ata gat att      1872
Glu Val Thr Glu Leu Asn Asn Tyr Asn Ile Lys Leu His Ile Asp Ile
    610             615             620 act aat taa                                                           1881
Thr Asn
```

<210> SEQ ID NO 7
<211> LENGTH: 10
<212> TYPE: PRT
<213> ORGANISM: Artificial
<220> FEATURE:
<223> OTHER INFORMATION: synthetic peptide

<400> SEQUENCE: 7

Met Asp Tyr Lys Asp Asp Asp Asp Lys Leu
1               5                   10

<210> SEQ ID NO 8
<211> LENGTH: 24
<212> TYPE: PRT
<213> ORGANISM: Artificial
<220> FEATURE:
<223> OTHER INFORMATION: synthetic peptide

<400> SEQUENCE: 8

Met Ala Ser Trp Ser His Pro Gln Phe Glu Lys Gly Ala Leu Glu Val
1               5                   10                  15

Leu Phe Gln Gly Pro Gly Tyr Gln
            20

<210> SEQ ID NO 9
<211> LENGTH: 31
<212> TYPE: DNA
<213> ORGANISM: Artificial
<220> FEATURE:
<223> OTHER INFORMATION: primer

<400> SEQUENCE: 9
cactataagc ttatccaaaa ttcattaaat g                              31

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
gttgataggt accttatggg ttactcatag                                30

<210> SEQ ID NO 11
<211> LENGTH: 30
<212> TYPE: DNA
<213> ORGANISM: Artificial
<220> FEATURE:
<223> OTHER INFORMATION: primer

<400> SEQUENCE: 11
tgaataagct ttcagctgaa agaactttc                                 30

<210> SEQ ID NO 12
<211> LENGTH: 32
<212> TYPE: DNA
<213> ORGANISM: Artificial
<220> FEATURE:
<223> OTHER INFORMATION: primer

<400> SEQUENCE: 12
cactttggta ccttatattt tttcaagttt ga                             32

```
<210> SEQ ID NO 13
<211> LENGTH: 31
<212> TYPE: DNA
<213> ORGANISM: Artificial
<220> FEATURE:
<223> OTHER INFORMATION: primer

<400> SEQUENCE: 13
gaaaaagggt accaatatag tgatactatt g                              31

<210> SEQ ID NO 14
<211> LENGTH: 31
<212> TYPE: DNA
<213> ORGANISM: Artificial
<220> FEATURE:
<223> OTHER INFORMATION: primer

<400> SEQUENCE: 14
cgtgtcgact taattagtaa tatctatatg c                              31
```

ADJUVANT FOR MUCOSAL VACCINE

CROSS-REFERENCE TO RELATED APPLICATIONS

This application is a Continuation of U.S. application Ser. No. 14/649,279, which is the U.S. National Stage application of PCT/JP2013/081459, filed Nov. 15, 2013, which claims priority from Japanese application JP 2012-265532, filed Dec. 4, 2012.

The instant application contains a Sequence Listing which has been submitted in ASCII format via EFS-WEB and is hereby incorporated by reference in its entirety. Said ASCII copy, created on Jul. 27, 2016, is named sequence.txt and is 27 KB.

TECHNICAL FIELD

The present invention relates to an effective and safe adjuvant for a mucosal vaccine and a mucosal vaccine preparation containing such adjuvant and vaccine antigens.

BACKGROUND ART

In recent years, the mechanisms of mucosal immunity on the respiratory apparatus, the digestive apparatus, the reproductive organs, and other organs have been gradually elucidated as the immune system to prevent infectious diseases such as influenza or acquired immunodeficiency syndrome (AIDS). For example, immune response to prevent influenza virus infection is associated with mucosal IgA antibody, serum IgG antibody to neutralize the viruses, and cytotoxic T cells that lyse infected cells to interrupt virus transmission. Such mucosal immune mechanisms are functional at the initial phase of infection, and play a key role in biophylaxis at the time of infection or during the initial phase of infection. Accordingly, mucosal vaccines inducing immune protection response against infection on the mucosa, which is the first barrier at portals of entry for pathogens, are considered as effective vaccine for various infectious diseases through mucosae.

While mucosal vaccines induce secretory IgA antibody in mucosal tissue upon mucosal administration (e.g., intranasal administration), and also induce IgG antibody in the serum. Thus, mucosal vaccines are capable of inducing immune responses in both the mucosal and systemic systems against pathogens. In addition, mucosal vaccines are superior to conventional vaccination with needles and syringe in terms of operability, safety, and economic efficiency. Accordingly, mucosal vaccines are expected as novel vaccines, and have been developed.

However, because mucosal vaccines with antigens alone are not capable of inducing sufficient immune responses, mucosal adjuvants for mucosal vaccines is necessary in order to induce effective immune responses on the mucosal surface. Up to the present, many mucosal adjuvants have been reported. For example, bacterial endotoxins such as *cholera* toxin (CT) and heat-labile enterotoxin (LT) of enterotoxigenic *Escherichia coli*, have been known as representative mucosal adjuvants (Non-Patent Documents 1 and 2). However, previous reports showed that clinical trials with LT intranasal administration caused facial nerve palsy (Bell's palsy). Accordingly, development of mucosal adjuvants with toxins such as CT or LT might be difficult in terms of safety. MPL resulting from attenuation of activity of endotoxin LPS, bacterial flagellin proteins (Patent Document 1), double-stranded RNA (poly(I:C)) (Patent Document 2), and other substances have been studied as mucosal adjuvants, which are not derived from toxins. However, since those candidates induce excessive inflammatory responses, they are not satisfactory for mucosal adjuvants in terms of safety. That is, no effective and safe adjuvants for mucosal vaccines are being put to practical use at present.

The hemagglutinin (HA) and the nontoxic-nonhemagglutinin (NTNH) component bind to the *botulinum* neurotoxin (NTX) produced by *botulinum bacilli* causing food poisoning, and those components form three types of neurotoxin complex (progenitor toxin (PTX)) whose molecular weight are 300,000, 500,000, or 900,000. Botulinum toxin blocks neuron transmission, and leads to death in human. Taking advantage of the activity thereof, *botulinum* toxin is used as an effective neurotransmission inhibitor for medical purposes. For example, a *botulinum* toxin type A (BOTOX) complex is known to be used for treatment of blepharospasm, hemifacial spasm, spasmodic torticollis, heterotropia, and the reduction of wrinkles. In the neurotoxin complex as described above, non-toxic HA is known to have functions of disrupting the epithelial barrier and transporting *botulinum* neurotoxins and macromolecules. When NTX and albumin antigens are subcutaneously administered to mice in combination with HA, production of serum antibody specific for antigens is enhanced through IL-6 production (Non-Patent Document 3). While Patent Documents 3 and 4 describe the adjuvant activity of an HA subcomponent (HA1 or HA3) and the use as a carrier of nucleic acids into cells, no protein complex composed of HA subcomponents (HA1, HA2, and HA3) has been discussed. The present inventors previously reported that HA acts on M cells in the epithelial cell layer of the Peyer's patch (i.e., M cells on the Peyer's patch), and that HA assists migration of neurotoxin complex from apical side of to basolateral side of M cells via transcytosis (Non-Patent Document 4). While the functions of the neurotoxin complex (HA to which the toxin component has been bound) to breach the intestinal epithelial barrier have been investigated in the study described above, interaction of toxin-free HA with M cells or adjuvant effects for delivering vaccine antigens for mucosal vaccines to infectious diseases have not yet been examined.

PRIOR ART DOCUMENTS

Patent Documents

Patent Document 1: WO 2005/070455
Patent Document 2: JP 2005-97267 A
Patent Document 3: JP 2009-132686 A
Patent Document 4: JP 2009-81997 A

Non-Patent Documents

Non-Patent Document 1: J. Xu-Amano et al., J. Exp. Med., 178, 1309, 1993
Non-Patent Document 2: I. Takahashi et al., J. Infect. Dis. 173, 627, 1996
Non-Patent Document 3: J. Lee et al., Microbiology, 151, 3739, 2005
Non-Patent Document 4: Takuhiro Matsumura et al., Japanese Journal of Bacteriology 64 (1) 79, 2009

SUMMARY OF THE INVENTION

Accordingly, an object of the present invention is to provide an adjuvant for mucosal vaccines with high both efficacy and safety.

The present inventors focused on hemagglutinin (HA), a non-toxic component of *botulinum* toxin, and the mice were intranasally immunized with a protein complex composed of HA subcomponents (HA1, HA2, and HA3) intranasal in combination with ovalbumin antigens or influenza HA antigens. As a result, they confirmed that production of serum IgG antibody and that of secretory IgA antibody on the mucosa would be accelerated by vaccine antigens with HA subcomponent, suggesting that HA augments systemic immunity and mucosal immunity to vaccine antigens. In addition, innate immunity (e.g., production of IL-6) caused by CpG or LPS would not be affected by additional HA. Thus, they discovered that the HA complex would be effective as an adjuvant for a mucosal vaccine without induction of inflammation.

The present invention includes the following.

(1) An adjuvant for a mucosal vaccine comprising a protein complex composed of hemagglutinin (HA) subcomponents HA1, HA2, and HA3 of *botulinum* toxin.
(2) The adjuvant according to (1), wherein the protein complex is composed of the first component, the second component, and the third component described below: the first component:
  (a) a protein consisting of the amino acid sequence as shown in SEQ ID NO: 1, or
  (b) a protein consisting of an amino acid sequence derived from the amino acid sequence as shown in SEQ ID NO: 1 by deletion, substitution, or addition of one to several amino acids and having functions equivalent to those of the protein (a); the second component:
  (c) a protein consisting of the amino acid sequence as shown in SEQ ID NO: 2, or
  (d) a protein consisting of an amino acid sequence derived from the amino acid sequence as shown in SEQ ID NO: 2 by deletion, substitution, or addition of one to several amino acids and having functions equivalent to those of the protein (c); and the third component:
  (e) a protein consisting of the amino acid sequence as shown in SEQ ID NO: 3, or
  (f) a protein consisting of an amino acid sequence derived from the amino acid sequence as shown in SEQ ID NO: 3 by deletion, substitution, or addition of one to several amino acids and having functions equivalent to those of the protein (e).
(3) The adjuvant according to (1) or (2), which is used simultaneously with vaccine antigens or before or after vaccine antigens are administered.
(4) The adjuvant according to (3), wherein the vaccine antigens are subunit antigens or inactivated antigens.
(5) The adjuvant according to (3) or (4), wherein the vaccine antigens are derived from pathogens causing mucosal infections.
(6) The adjuvant according to (5), wherein the pathogens causing mucosal infections are viruses or bacteria.
(7) The adjuvant according to (6), wherein the viruses are influenza viruses, human immunodeficiency viruses (HIV), chickenpox viruses, measles viruses, rubella viruses, mumps viruses, polioviruses, rotaviruses, adenoviruses, herpes viruses, RS viruses, dengue viruses, Japanese encephalitis viruses, severe acute respiratory syndrome (SARS) viruses, or hepatitis viruses (type A, type B, or type C).
(8) The adjuvant according to (6), wherein the bacteria are *Bordetella pertussis*, *Neisseria meningitidis*, type B influenza, pneumococcus, tuberculosis bacteria, tetanus bacilli, or *cholera bacilli*.
(9) The adjuvant according to any of (1) to (8), which is administered with any mucosal routes.
(10) The adjuvant according to (9), wherein the administration with mucosal routes is intranasal administration.
(11) A mucosal vaccine preparation comprising vaccine antigens and the adjuvant according to any of (1) to (10).

When the adjuvant of the present invention is administered to mucosa such as the intranasal mucosa in combination with vaccine antigens derived from pathogens causing mucosal infections, such as influenza viruses, production of serum IgG antibody and that of secretory IgA antibody on the mucosa are accelerated, and antigen-specific systemic and mucosal immune responses are enhanced. Accordingly, the adjuvant of the present invention is useful as an adjuvant for a mucosal vaccine against diseases of the respiratory apparatus or the digestive apparatus. In addition, the adjuvant of the present invention uses hemagglutinin (HA) subcomponent, which is a non-toxic *botulinum* toxin component, the adjuvant does not activate innate immunity, and the adjuvant is less likely to cause inflammations on mucosa after administration. Therefore, the adjuvant of the present invention is very safe for mucosal vaccines to use.

This patent application claims priority from Japanese Patent Application No. 2012-265532 filed on Dec. 4, 2012, and it includes part or all of the contents as disclosed in the description thereof.

BRIEF DESCRIPTION OF THE DRAWINGS

FIG. 1 shows the amino acid sequence of recombinant *botulinus* HA1-3 used to prepare the *botulinus* HA (BHA) complex in Example 1. The underlined regions indicate vector-derived amino acid sequences (FLAG tag sequence: SEQ ID NO: 7; Strep tag sequence: SEQ ID NO: 8).

EMBODIMENTS FOR CARRYING OUT THE INVENTION

Figure 2:
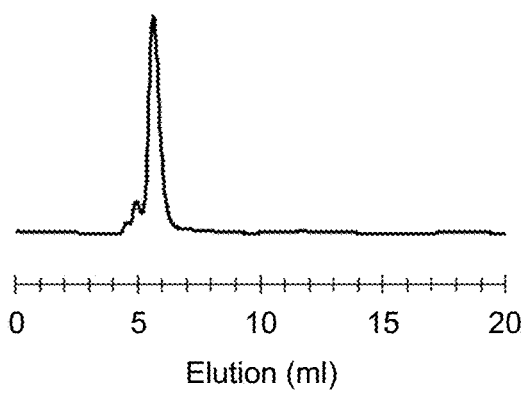
FIG. 2 shows purification of the BHA complex via gel filtrationchromatography.

The adjuvant for a mucosal vaccine of the present invention (hereafter it is merely referred to as an "adjuvant") is a protein complex composed of HA1, HA2, and HA3, which are hemagglutinin (HA) subcomponents of *botulinum* toxin. The term "adjuvant" used herein refers to a substance that is administered so as to enhance the immunogenicity of a vaccine antigen.

Botulinum toxins are classified as type A to type G in accordance with the different antigenicities of toxins produced by *botulinum bacilli* (*Clostridium botulinum*). The *botulinum* toxin complex for the adjuvant of the present invention is preferably of type A or type B.

The first component of the protein complex contained in the adjuvant of the present invention is the *botulinum* toxin complex HA1, the second component is the *botulinum* toxin complex HA2, and the third component is the *botulinum* toxin complex HA3. Specifically, HA1, HA2, and HA3 are a protein consisting of the amino acid sequence as shown in SEQ ID NO: 1, a protein consisting of the amino acid sequence as shown in SEQ ID NO: 2, and a protein consisting of the amino acid sequence as shown in SEQ ID NO: 3, respectively. The adjuvant of the present invention is preferably a protein complex composed of the first component, the second component, and the third component.

The three proteins composing the protein complex may be mutant proteins of the protein consisting of the amino acid sequence as shown in SEQ ID NO: 1, the protein consisting of the amino acid sequence as shown in SEQ ID NO: 2, and the protein consisting of the amino acid sequence as shown in SEQ ID NO: 3, respectively, provided that such mutant proteins have activities equivalent to those of the relevant original proteins. When mutant proteins "have activities equivalent to" those of the original proteins, the protein complex composed of such mutant proteins has mucosal adjuvant activity equivalent to that of the protein complex composed of the protein consisting of the amino acid sequence as shown in SEQ ID NO: 1, the protein consisting of the amino acid sequence as shown in SEQ ID NO: 2, and the protein consisting of the amino acid sequence as shown in SEQ ID NO: 3. The term "mucosal adjuvant activity" refers to activity that enhances production of antigen-specific antibody when the adjuvant is administered transmucosally in combination with vaccine antigens in both the mucosal and systemic immune response. Preferably, the influence of such activity on innate immunity is insignificant, and production of antigen-specific antibody is enhanced in both the mucosal and systemic immunity. More preferably, innate immunity is not influenced and production of antigen-specific antibody is enhanced in both the mucosal and systemic immunity. An example of such mutant protein is a protein consisting of an amino acid sequence derived from the amino acid sequence as shown in SEQ ID NO: 1, 2, or 3 by deletion, substitution, insertion, or addition of one to several amino acids. The term "one to several" used herein indicates the number of amino acids that can be deleted, substituted, or added by a known method for producing a mutant protein, such as site-directed mutagenesis. As long as the activity described above is retained, such number is not limited. For example, such number is 1 to 30, preferably 1 to 20, more preferably 1 to 10, and most preferably 1 to 5. A mutant protein may consist of an amino acid sequence having 90% or higher identity to the amino acid sequence as shown in SEQ ID NO: 1, 2, or 3. The term "90% or higher identity" used herein refers to sequence identity of preferably 95% or higher, more preferably 97% or higher, and most preferably 98% or higher. Amino acid sequence identity can be determined by FASTA or BLAST search. While the term "mutation" used herein primarily refers to a mutation that is artificially introduced in accordance with a known method of producing a mutant protein, an equivalent mutation existing in nature may be employed.

A method for producing the adjuvant of the present invention is not particularly limited. The protein complex may be derived from nature. Alternatively, proteins composing such protein complex may be produced via a genetic recombination technique, and the protein complex may be formulated using such proteins. The protein complex may be produced in accordance with a conventional genetic recombination technique using genes encoding the proteins of interest. Specifically, HA1, HA2, and HA3 can be produced by constructing expression vectors containing genes encoding the amino acid sequences as shown in SEQ ID NOs: 1, 2, and 3 (the nucleotide sequences are shown in SEQ ID NOs: 4, 5, and 6, respectively), introducing the expression vectors into adequate host cells, and culturing the host cells. Mutant proteins of HA1, HA2, and HA3 can be also produced by a well-known recombinant DNA technique by, for example, subjecting genes encoding the amino acid sequences as shown in SEQ ID NOs: 1, 2, and 3 to site-directed mutagenesis, obtaining genes encoding the mutant proteins, and using such genes. The protein productions can be easily carried out with reference to, for example, Molecular Cloning 2nd Ed., Cold Spring Harbor Laboratory Press, 1989. Alternatively, HA1, HA2, and HA3 can be chemically synthesized on the basis of the amino acid sequences thereof.

The resulting HA1, HA2, and HA3 proteins may be incubated in a solvent such as a phosphate buffer for 2 to 8 hours, preferably 3 to 5 hours, and more preferably 3 hours at 25° C. to 40° C., and preferably 37° C., and the protein complex may be thus composed. Alternatively, a fusion protein may be prepared from the HA1, HA2, and HA3 proteins. When production of a fusion protein is intended, a known method in which DNA fragments encoding the HA1, HA2, and HA3 proteins are bound to be in-frame with each other, the resultant is introduced into an adequate expression vector, and the resultant is transcribed and translated with the aid of an adequate host so as to express the protein may be employed.

In general, the adjuvant of the present invention may be administered to organisms simultaneously with vaccine antigens. Alternatively, the adjuvant may be administered before the administration of vaccine antigens or after the administration of antigens. When the adjuvant is administered simultaneously with vaccine antigens, the adjuvant may be administered substantially simultaneously with the vaccines. For example, the adjuvant and vaccine antigens may be administered to the target at exactly the same time, or they may be continuously administered within a given period of time (preferably within several minutes).

The vaccine antigens are preferably inactivated antigens or subunit antigens. The term "inactivated antigens" refers to antigens of pathogens (e.g., viruses or bacteria) deprived of infectivity. Examples thereof include complete virus particles (virions), incomplete virus particles, virion-constituting particles, virus nonstructural proteins, the antigens to prevent infections, and neutralizing epitopes. Antigens may be inactivated by physical treatments (e.g., x-rays, heat, or ultrasound), chemical treatments (e.g., formalin, mercury, alcohol, or chlorine), or via other means. The term "subunit vaccines" refers to vaccines selectively containing particular antigens (i.e., the antigens to prevent infections) that are effective vaccine components among various types of antigens contained in inactivated vaccines. An example of a subunit vaccine against the influenza virus is a vaccine selectively containing hemagglutinin (HA) and neuraminidase (NA) that are surface antigens purified.

The vaccine antigens are not particularly limited, provided that the vaccine antigens are capable of inducing a mucosal immune response together with the adjuvant of the present invention. Typical antigens are derived from pathogens causing mucosal infections. Pathogens causing mucosal infections may be viruses or bacteria. Examples of viruses include, but are not limited to, influenza viruses, human immunodeficiency viruses (HIV), chickenpox viruses, measles viruses, rubella viruses, mumps viruses, polioviruses, rotaviruses, adenoviruses, herpes viruses, RS viruses, dengue viruses, Japanese encephalitis viruses, severe acute respiratory syndrome (SARS) viruses, and hepatitis viruses (type A, type B, and type C). Examples of bacteria include, but are not limited to, *Bordetella pertussis, Neisseria meningitidis*, type B influenza, pneumococcus, tuberculosis bacteria, tetanus bacilli, and *cholera bacilli*. Such antigens derived from pathogens may be derived from nature or artificially prepared via gene recombination or other techniques.

The vaccine antigens include allergens used for hyposensitization therapy. Accordingly, the adjuvant of the present invention can be used as an adjuvant for allergen vaccines. Allergen vaccines are used to block IgE causing allergies by producing IgG antibody against allergens or to increase allergen-specific type I helper T cells (Th1 cells) in vivo by administering allergens to organisms, thereby decreasing type II helper T cells (Th2 cells) associated with allergy symptoms. Allergen vaccines are capable of suppressing allergy symptoms via hyposensitization. Allergens are not particularly limited, and examples of allergens include food allergens (e.g., casein, lactalbumin, lactoglobulin, ovomucoid, ovalbumin, and conalbumin), house dust allergens (e.g., mite allergens), pollen allergens (e.g., cedar pollen allergens, ragweed allergens, and cocksfoot grass allergens), and allergens of animal body hair.

The adjuvant of the present invention is administered transmucosally in combination with the mucosal vaccine antigens. When an agent is "administered transmucosally," it is administered through the mucosa. Examples of mucosae include inner walls of hollow organs that lead to the exterior, such as the digestive apparatus, the respiratory apparatus, and the urogenital apparatus, and specific examples include the nasal cavity, oral cavity, pharynx, alveolus, air tube, intestinal tract, and vagina, with the nasal cavity being preferable. Accordingly, examples of forms of transmucosal administration include intranasal, intraoral, intra-alveolar, intratracheal, intravaginal, and intrarectal administration with the intranasal administration being preferable. Adjuvants and mucosal vaccines can be administered transmucosally in an adequate manner in accordance with the site of administration. In the case of nasal or oral administration, for example, the agents can be sprayed, added dropwise, or applied to the nasal cavity or oral cavity. Intra-alveolar administration can be carried out by a method involving the use of an inhaler or a sprayer or a method of administering a preparation comprising an aerosol preparation.

The amount of the adjuvant of the present invention to be administered varies in accordance with the age of the subject, body weight, disease type, route of administration, form of administration, and other conditions. In the case of oral administration, for example, 10 μg to 100 mg, and preferably 1 μg to 10 mg of the adjuvant of the present invention can be administered simultaneously with vaccine antigens per instance per adult human. In the case of nasal administration, 0.1 μg to 100 mg, and preferably 1 μg to 10 mg of the adjuvant can be administered, for example. Subjects of administration can be adequately determined in accordance with the types of vaccine antigens used in combination with the adjuvant. Examples thereof include, in addition to humans, non-human mammalians, birds, and crustaceans.

A person skilled in the art can easily determine the frequency of administration of the adjuvant of the present invention in combination with vaccine antigens to the subjects by taking, for example, age, body weight, medical history, clinical course of the subject, disease type, and other factors into consideration. As in the case of general vaccine preparations, administration may be carried out at an adequate time before the onset of the disease at the frequency of, in general, one to several instances per day for a day, or administration may be carried out several times at intervals of one to several weeks. Administration is preferably carried out while observing progress, and booster immunization is preferably carried out at intervals of at least a week. Intervals of booster immunization are preferably at least about two weeks. By providing booster immunization, more effective infection-protective effects can be expected.

In order to administer the adjuvant of the present invention simultaneously with vaccine antigens, the adjuvant may be mixed with vaccine antigens together with pharmaceutically acceptable carriers suitable for the dosage form, and vaccine preparations may be produced by various known techniques.

The amount of the adjuvant to be incorporated into vaccine preparations can be adequately determined in accordance with the types of vaccine antigens to be mixed. The content of the adjuvant in the preparations is not particularly limited, provided that sufficient antigen immune responses are induced via transmucosal administration. Such amount is generally 0.1% to 90% by weight, preferably 0.5% to 80% by weight, and more preferably 1% to 50% by weight relative to the entire preparation amount.

Dosage forms of the mucosal vaccine preparations of the present invention are not particularly limited, provided that the mucosal vaccine preparations can be administered transmucosally. Examples thereof include liquid preparations, suspensions, sprays, and powders. According to need, various additives that are generally used for vaccine preparations, such as solubilizers, anticoagulants, viscosity modifiers, pH adjusters, isotonizing agents, emulsifiers, antioxidants, fillers, surfactants, diluents, preservatives, stabilizers, desiccating agents, or moisturizing agents, can be added to the mucosal vaccine preparations of the present invention.

The vaccine preparations of the present invention can be in a liquid state or a dried state, and such vaccine preparations can be introduced into hermetically sealed vial bottles, syringes, atomizers, or sealed ampules.

Hereafter, the present invention is described in greater detail with reference to the examples, although the technical scope of the present invention is not limited thereto. The data obtained in the examples were statistically processed by the Student's t-test.

EXAMPLE 1

Preparation of *Botulinus* HA (BHA) Complex

The *botulinus* HA (BHA) complex was prepared in the manner described below.

(1) Preparation of Plasmids

The genes encoding the proteins of the *botulinus* HA subcomponents (BHA1, BHA2, and BHA3) (BHA1: a protein consisting of amino acids 7 to 294 of the amino acid sequence as shown in SEQ ID NO: 1; BHA2: a protein consisting of amino acids 2 to 146 of the amino acid sequence as shown in SEQ ID NO: 2; and BHA3: a protein consisting of amino acids 19 to 626 of the amino acid sequence as shown in SEQ ID NO: 3) were amplified by PCR from genomic DNA of the *Clostridium botulinum* B-Okra strain as a template using the primers described below.

```
(Primers for BHA1 amplification)
BHA1 forward primer:
                              (SEQ ID NO: 9)
cactataagcttatccaaaattcattaaatg BHA1 reverse primer:
                              (SEQ ID NO: 10)
gttgataggtaccttatgggttactcatag (Primers for BHA2 amplification)
BHA forward primer:
                              (SEQ ID NO: 11)
tgaataagctttcagctgaaagaactttc BHA2 reverse primer:
                              (SEQ ID NO: 12)
cactttggtaccttatatttttcaagtttga
```

```
(Primers for BHA3 amplification)
BHA3 forward primer:
                              (SEQ ID NO: 13)
gaaaaagggtaccaatatagtgatactattg BHA3 reverse primer:
                              (SEQ ID NO: 14)
cgtgtcgacttaattagtaatatctatatgc
```

The amplified DNA fragments of BHA1 and BHA2 were each inserted into the HindIII-SalI site of pT7-FLAG-1 (Sigma), and the amplified DNA fragment of BHA3 was inserted into the KpnI-SalI site of pET52b(+) (Novagen) (pET-BHA3).

(2) Protein Expression

The resulting plasmids were separately transformed into *E. coli* Rosetta2 (DE3) strains (Novagen). Protein expression was induced using the Overnight Express Autoinduction System 1 (Novagen). BHA1 and BHA3 were induced to express proteins at 30° C. for 36 hours, and BHA2 was induced to express a protein at 18° C. for 40 hours. *E. coli* strains were collected by centrifugation and stored at −80° C.

(3) Protein Purification and Complex Preparation

BHA1 and BHA2 were purified using Anti-FLAG M2 agarose (Sigma). BHA3 was purified using StrepTrap HP (GE Healthcare). The amino acid sequences of the purified recombinant proteins, FLAG-BHA1, FLAG-BHA2, and Strep-BHA3, are shown in FIG. 1.

The purified recombinant proteins were mixed at a ratio of BHA1:BHA2:BHA3 of 4:4:1 by mole, and the resultant was incubated at 37° C. for 3 hours, followed by purification with the use of StrepTrap HP. Thus, the BHA complex (BHA) was obtained.

(4) Gel Filtration Chromatography of *Botulinus* HA (BHA) Complex

The BHA complex (BHA) prepared in Example 1 was separated using Superdex 200 10/300 GL (GE Healthcare). In this test, C-terminal FLAG tag HAL N-terminal His tag HA2, and N-terminal Strep tag HA3 were used for HA1, HA2, and HA3 composing the BHA complex (BHA). The results are shown in FIG. 2.

EXAMPLE 2

Figure 3:
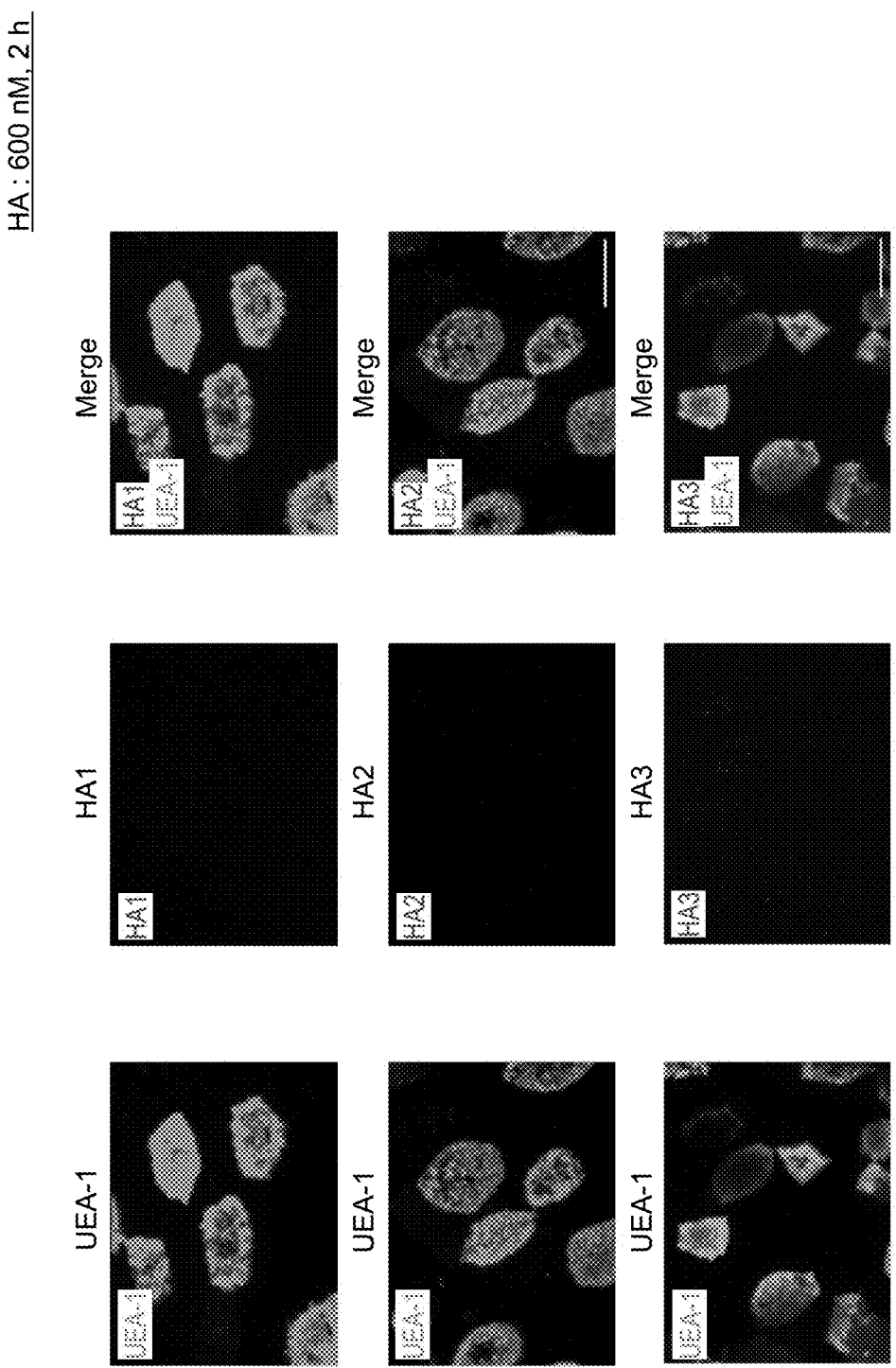
FIG. 3 shows interaction between M cells and each subcomponent HA1, HA2, or HA3 of *botulinus* (a microscope photograph showing localization of subcomponents on the follicle-associated epithelium (FAE)).

Interaction Between M Cell and *Botulinus* HA Subcomponent Alone or Complex of *Botulinus* HA Subcomponents HA1, HA2, and HA3 of *botulinus* type A (600 nM each) were labeled with Alexa 568 and injected into ligated intestinal loop of the mouse. Two hours later, HA subcomponent localization was observed under a confocal microscope. M cells were stained with FITC-labeled UEA-1. Neither M-cell binding nor transcytosis was substantially observed as a result when HA1, HA2, or HA3 alone was used (FIG. 3).

Figure 4:
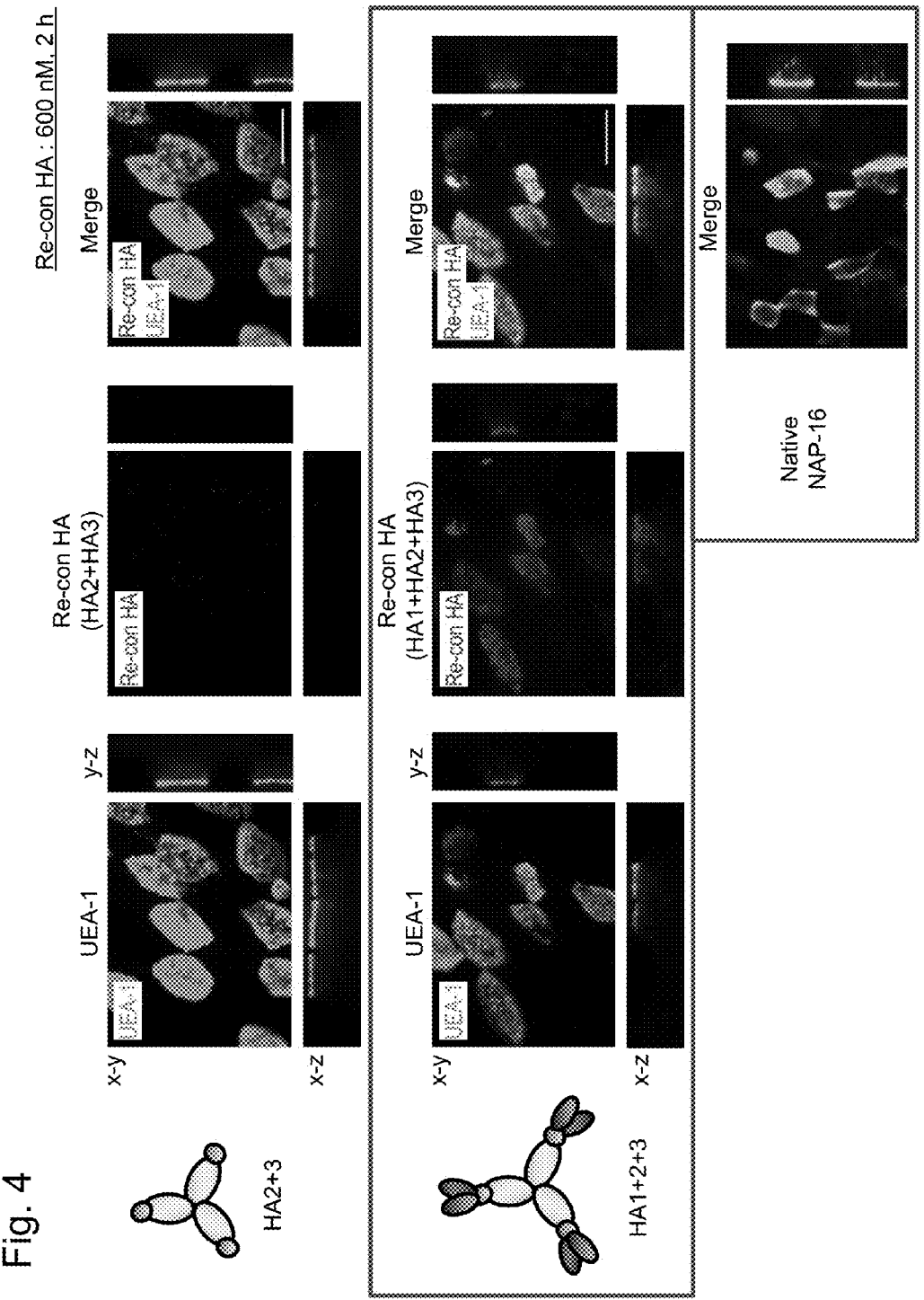
FIG. 4 shows interaction between M cell and the HA2+3 complex or the HA1+2+3 complex of *botulinus* (a microscope photograph showing localization of complexes on the follicle-associated epithelium (FAE)).
Figure 5:
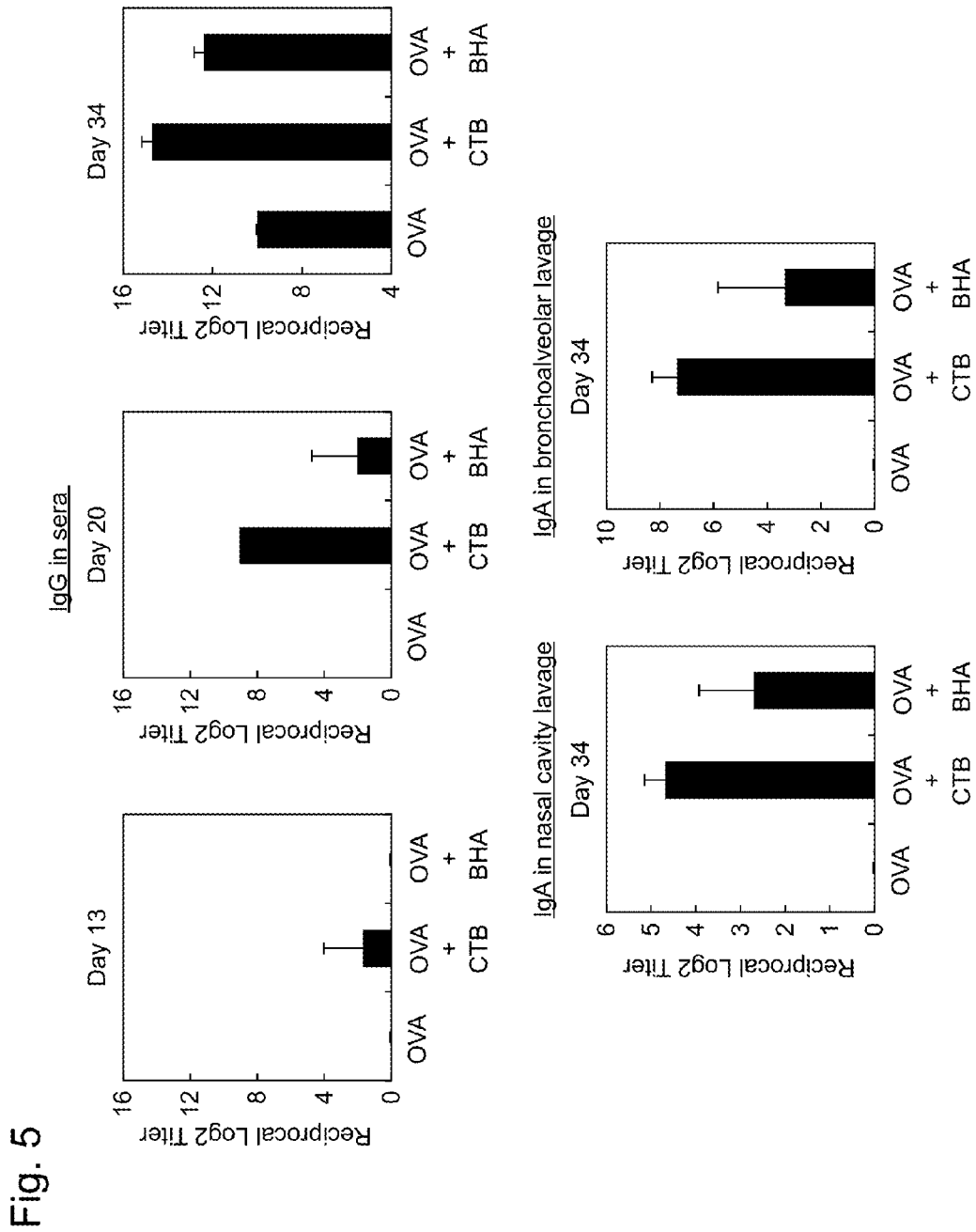
FIG. 5 shows the results of ELISA that measured the concentration of ovalbumin-specific IgG in sera and that of ovalbumin-specific IgA in the nasal cavity lavage or in the bronchoalveolar lavage (OVA: the group to which ovalbumin alone is administered; OVA+CTB: the group to which ovalbumin with the *cholera* toxin B subunit are administered; OVA+BHA: the group to which ovalbumin with the BHA complex are administered; Reciprocal log 2 titer: the antibody titer represented by the logarithm of the reciprocal of the maximal dilution factor exhibiting absorbance that is higher than the sample before immunization by 0.1).
Figure 6:
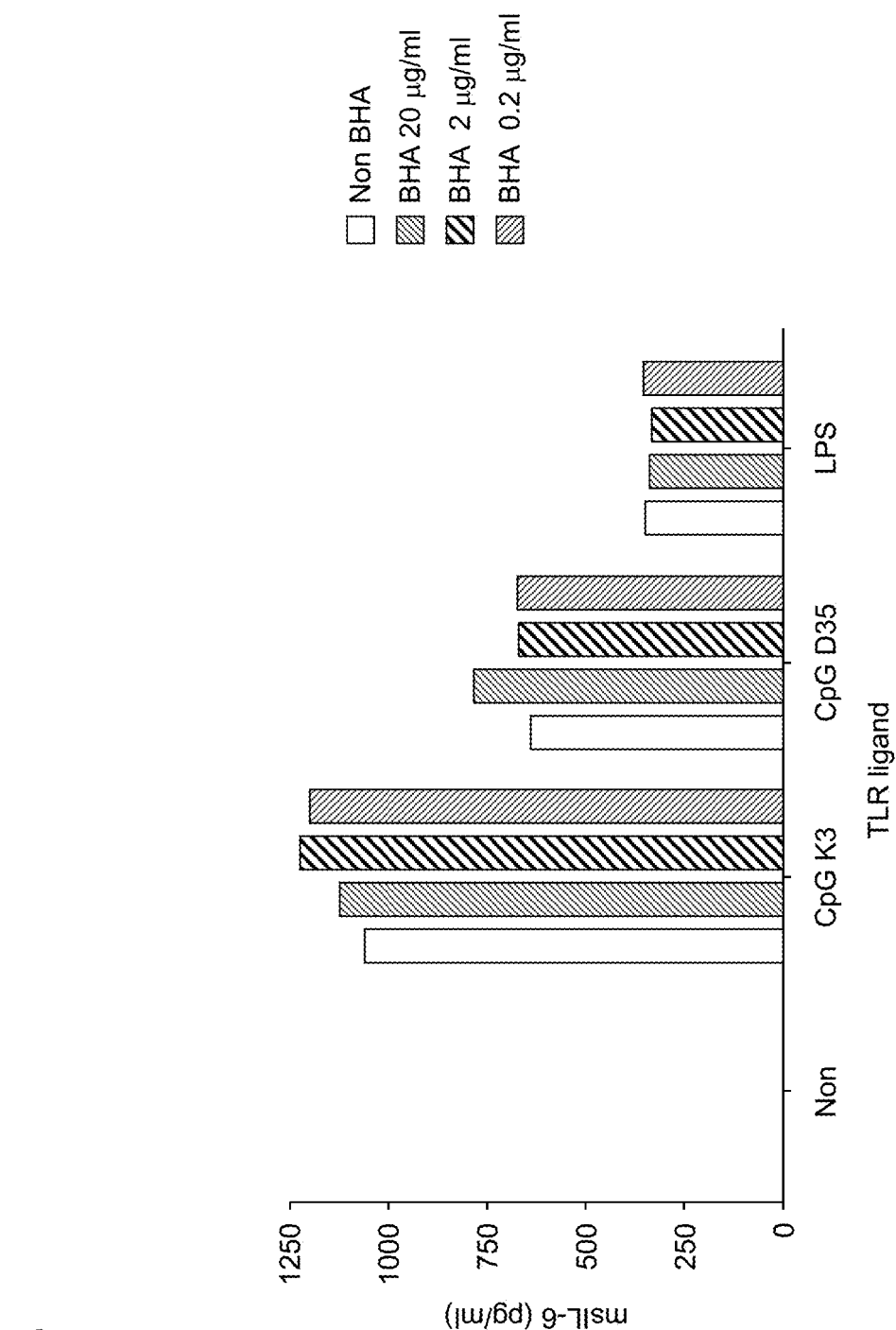
FIG. 6 shows activation of innate immunity by the BHA complex (the amount of IL-6 produced).

Separately, the HA2+3 complex and the HA1+2+3 complex of *botulinus* type A (600 nM each) were labeled with Alexa 568 and injected into ligated intestinal loop of the mouse. Two hours later, localization of complexes was observed under a confocal microscope. M cells were stained with FITC-labeled UEA-1. Neither M-cell binding nor transcytosis was substantially observed as a result when the HA2+3 complex was used. As with the case of native 16S toxin, M-cell binding and transcytosis were observed when the HA1+2+3 complex was used (FIG. 4). Thus, formation of a complex of HA1, HA2, and HA3 was found to be necessary for interaction between M cell and HA.

EXAMPLE 3

Nasal Adjuvant Effects of BHA Complex Using Ovalbumin (OVA)

With the use of model antigens (ovalbumin, OVA), the efficacy of *botulinus* HA (BHA) as a mucosal vaccine adjuvant was inspected in the mouse with intranasal administration system. The BHA complex (BHA) prepared in Example 1 was used as BHA. OVA (5 μg only), OVA (5 μg)+BHA (15 μg), and OVA (5 μg)+cholera toxin B subunit (2 μg) (as the positive control) were intranasally administered to BALB/c mice (6-week-old; a group of 3 individuals) at intervals of one week (at day 0, day 7, day 14, day 21, and day 28), and five times of administration was totally carried out. Production of OVA-specific IgG in the sera, that of OVA-specific IgA in the nasal cavity lavage, and that of OVA-specific IgA in bronchoalveolar lavage were assayed by ELISA on day 34.

The results are shown in FIG. 5. Production of IgA was not observed in any nasal cavity lavage or bronchoalveolar lavage in the group to which OVA alone had been administered, although a slight increase was observed in the sera IgG level on day 34. In the group to which OVA and BHA had been administered and the group to which OVA and the *cholera* toxin B subunit had been administered, the IgA levels in the nasal cavity lavage and the bronchoalveolar lavage and the amount of IgG in the sera significantly increased.

EXAMPLE 4

Evaluation of Ability of BHA Complex Adjuvant to Activate Innate Immunity (Activity to IL-6 Production)

The amount of IL-6 cytokine production resulting from treatment with the BHA complex adjuvant was measured using mouse splenocytes, and the ability of the BHA complex adjuvant to activate innate immunity was evaluated.

Splenocytes were sampled from native mice raised under SPF conditions (C57BL/6, 6-week-old, female, purchased from CLEA Japan, Inc.) and seeded onto a 96-well plate at a cell density of $1\times10^6$ cells/well. Thereafter, the BHA complex (BHA) was serially diluted from 20 μg/ml (20 μg/ml, 2 μg/ml, 0.2 μg/ml), and the splenocytes were stimulated. The splenocytes were further stimulated with the BHA complex adjuvant in combination with a TLR ligand of CpG oligo DNA (K3 or D35, 20 μg/ml) or LPS (1 μg/ml). The culture supernatant was recovered 24 hours after the initiation of stimulation and the amount of cytokine (IL-6) in the culture supernatant was measured (R&D systems). The results are shown in FIG. 6. As shown in FIG. 6, the induction of IL-6 by the BHA complex adjuvant alone was below the detection limit. The amounts of TNF-α, IL-1β, and IL-12 were also below the detection limit. Since the BHA complex adjuvant would not influence IL-6 production mediated by CpG or LPS stimulation, it was considered that the BHA complex adjuvant would not enhance or suppress signals to activate any other innate immunity. Thus, the BHA complex adjuvant was considered to be a non-inflammatory adjuvant that would not influence signals to activate innate immunity.

EXAMPLE 5

Effects of Intranasal Adjuvant of BHA Complex Using Influenza HA Antigens

Influenza split vaccines were used as antigens to evaluate adjuvant effects of the BHA complex.

(1) Experimental Animals and Materials

BALB/c mice and C57BL/6 mice (6-week-old, female) were purchased from CLEA Japan, Inc. Mice were raised under SPF conditions.

The mouse-adapted A/Puerto Rico/8/34 (H1N1) split vaccines (hereafter referred to as “split vaccines”) received from Kitasato Daiichi Sankyo Vaccine Co., Ltd. were used as vaccine antigens. During the experiment, antigens were refrigerated at 4° C. in the dark.

The BHA complex (BHA) prepared in Example 1 was used as the adjuvant. Endotoxin content was determined by designating the standard for purification at 0.5 EU/ml or lower. The BHA adjuvant was cryopreserved at −80° C., thawed immediately before use, and then used for immunization. The *cholera* toxin adjuvant (CTB) was prepared by mixing 1 μg of *cholera* toxin B subunit (Catalog No. 033-20611, Wako Pure Chemical Industries, Ltd.) and 1 μg of *cholera* toxin (Catalog No. 033-20621, Wako Pure Chemical Industries, Ltd.) for each mouse. The *cholera* toxin adjuvant was cryopreserved at −80° C., thawed immediately before use, and then used for immunization.

(2) Test Method

PBS(−) was added to the mixture of 1 μg of split vaccine antigens with 20 μg of the BHA complex (BHA) adjuvant or with 2 μg of the *cholera* toxin adjuvant to adjust the amount of each vaccine preparation to 12 μl used for each mouse. The vaccine preparations were administered to 6-week-old mice through both nasal cavities in amounts of 6 μl each. Administration was carried out four times in total at intervals of 2 weeks (day 0, day 14, day 28, and day 42). Immediately before booster immunizations were provided on day 14, day 28, and day 42, mice were anesthetized using Ketalar (Daiichi Sankyo Company, Limited)/Selactar (Bayer), and blood samples were obtained from the orbital venous plexus. The sampled blood was allowed to stand at 4° C., overnight, and serum separation was carried out using a refrigerated benchtop centrifuge (9,100 g, 10 minutes, 4° C.). The obtained serum specimens were cryopreserved at −20° C. In order to evaluate adjuvant effects of the BHA complex, IgG levels (total IgG, IgG1, IG2a, and IG2c levels) in the serum specimens were measured.

Mice were anesthetized using Ketalar/Selactar 56 days after the initiation of immunization, exsanguinated via cardiopuncture, and euthanized. Immediately thereafter, nasal cavity lavages and bronchoalveolar lavages were sampled. Thereafter, the nasal cavity lavages and the bronchoalveolar lavages were stored on ice or refrigerated until ELISA assays were initiated.

ELISA assays were carried out in the manner described below. The split vaccine antigens were applied to a plate at a concentration of 1 μg/ml (4° C., overnight), and blocking was carried out with 1% BSA/PBST (Tween 20: 0.5%) by allowing the plate to stand at room temperature for 2 hours. The serum sample was serially diluted using 1% BSA/PBST (Tween 20: 0.5%). As secondary antibody, HRP-labeled antibody in accordance with subclasses was used. OD was measured using a plate reader after coloring, and the amounts of influenza-antigen-specific antibody were calculated. The nasal cavity lavages and the bronchoalveolar lavages were serially diluted using 1% BSA/PBST (Tween 20: 0.5%). In order to evaluate adjuvant effects of the BHA complex to potentiate the antigen-specific mucosal immunity, the amount of influenza-antigen-specific mucosal IgA produced was measured.

(3) Test Results

Figure 7:
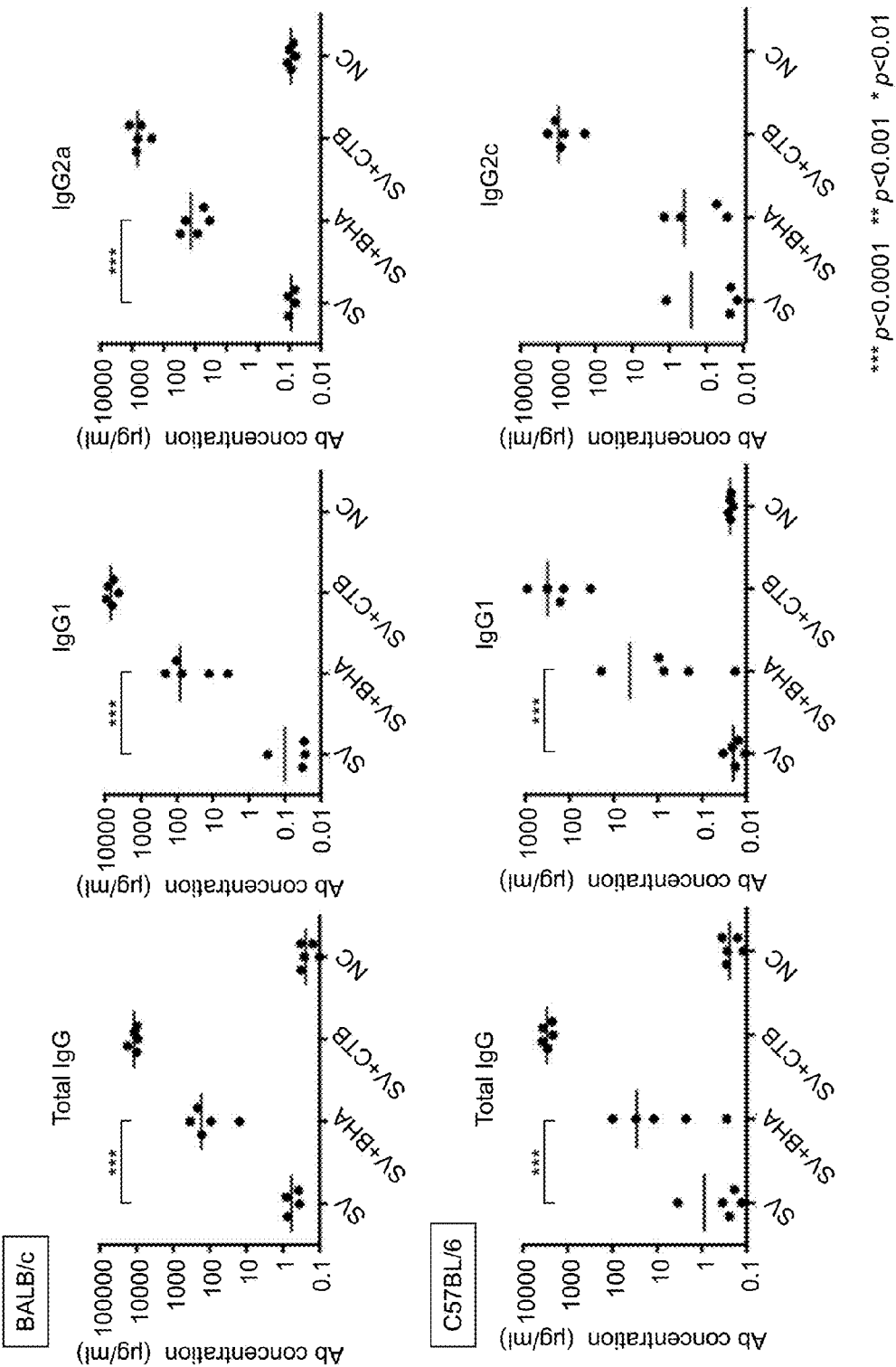
FIG. 7 shows the results of ELISA that measured the concentration of influenza-antigen-specific IgG in the sera (SV: the group to which influenza split vaccine alone is administered; SV+BHA: the group to which influenza split vaccine with BHA complex are administered; SV+CTB: the group to which influenza split vaccine with *cholera* toxin B subunit are administered; NC: the group to which no antigens with adjuvants is administered (*$p<0.0001$ $p<0.001$ *$p<0.01$)).

FIG. 7 shows the results of measurement of the level of influenza-antigen-specific IgG in the sera (56 days after the initiation of immunization).

As shown in FIG. 7, the level of the antigen-specific antibody reactions in the sera induced in the group subjected to immunization with the BHA complex (BHA) adjuvant in combination with the influenza antigens was significantly higher than that induced in the group subjected to immunization with influenza antigens alone. Such phenomenon was observed in all the evaluated IgG subclasses.

Figure 8:
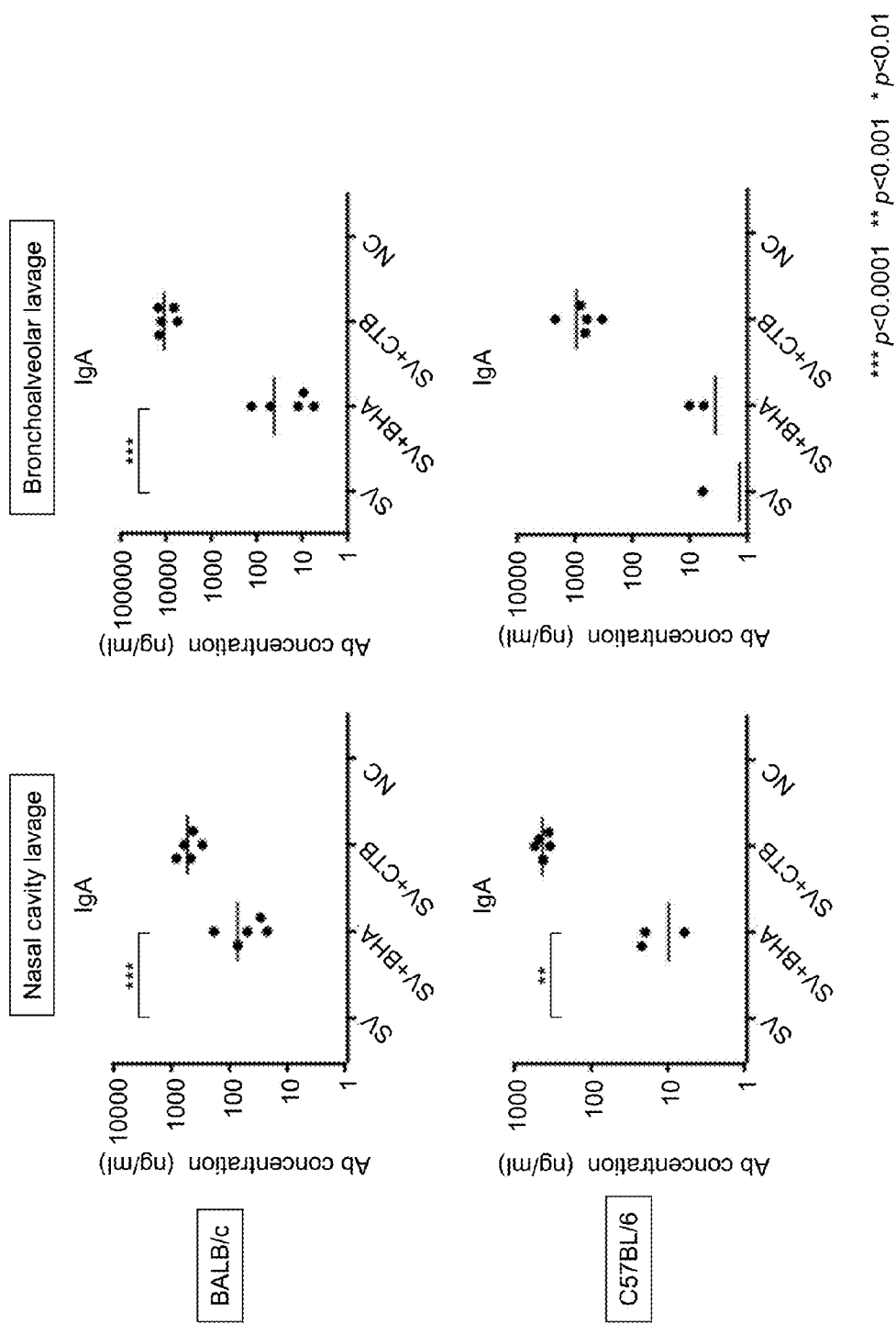
FIG. 8 shows the results of ELISA that measured the concentration of influenza-antigen-specific IgA in the nasal cavity lavage and in the bronchoalveolar lavage (SV: the group to which influenza split vaccine alone is administered; SV+BHA: the group to which influenza split vaccine with BHA complex are administered; SV+CTB: the group to which influenza split vaccine with *cholera* toxin B subunit are administered; NC: the group to which no antigens with adjuvants is administered (*$p<0.0001$ $p<0.001$ *$p<0.01$)).

FIG. 8 shows the results of measurement of the amount of secretory IgA produced in the nasal cavity lavages and in the bronchoalveolar lavages. As shown in FIG. 8, the amount of antigen-specific IgA production was high in the group subjected to immunization with the BHA complex (BHA) adjuvant in combination with the influenza antigens. In contrast, secretory IgA production was not substantially observed in the group of mice subjected to immunization with influenza antigens alone.

EXAMPLE 6

Comparison of Effects of Intranasal Adjuvants of BHA Complex with BHA1, BHA2, or BHA3 Respectively With the use of the influenza split vaccines as antigens, adjuvant effects of the BHA complex were compared with adjuvant effects of BHA1, BHA2, and BHA3 that are composing elements of the BHA complex.

(1) Experimental Animals and Materials

BALB/c mice (6-week-old, female) were purchased from CLEA Japan, Inc. Mice were raised under SPF conditions.

The mouse-adapted A/Puerto Rico/8/34 (H1N1) split vaccines (hereafter referred to as "split vaccines") received from Kitasato Daiichi Sankyo Vaccine Co., Ltd. were used as immunogens. During the experiment, antigens were refrigerated at 4° C. in the dark.

The BHA complex (BHA) prepared in Example 1 or BHA1, BHA2, and BHA3 that are composing elements of the BHA complex were used as the adjuvant. Endotoxin content was determined by designating the standard for purification at 0.5 EU/ml or lower. The BHA adjuvant was cryopreserved at −80° C., thawed immediately before use, and then used for immunization. The *cholera* toxin adjuvant (CTB) was prepared by mixing 1 µg of *cholera* toxin B subunit (Catalog No. 033-20611, Wako Pure Chemical Industries, Ltd.) and 1 µg of *cholera* toxin (Catalog No. 033-20621, Wako Pure Chemical Industries, Ltd.) for each mouse. The *cholera* toxin adjuvant was cryopreserved at −80° C., thawed immediately before use, and then used for immunization.

(2) Test Method

PBS(−) was added to the mixture of 1 µg of split vaccine antigens and 20 µg each of the BHA complex (BHA) adjuvant, the BHA1 adjuvant, the BHA2 adjuvant, or the BHA3 adjuvant or 2 µg of the CTB adjuvant to adjust the amount of each vaccine preparation to 12 µl used for each mouse. The vaccine preparations were administered to 6-week-old mice through both nasal cavities in amounts of 6 µl each. Administration was carried out four times in total at intervals of 2 weeks (day 0, day 14, day 28, and day 42).

Immediately before booster immunizations were provided on day 14, day 28, and day 42, mice were anesthetized using Ketalar (Daiichi Sankyo Company, Limited)/Selactar (Bayer), and blood samples were obtained from the orbital venous plexus. The sampled blood was allowed to stand at 4° C., overnight, and serum separation was carried out using a refrigerated benchtop centrifuge (9,100 g, 10 minutes, 4° C.). The obtained serum specimens were cryopreserved at −20° C. In order to evaluate adjuvant effects of the BHA complex, IgG levels (total IgG, IgG1, and IG2a levels) in the serum specimens were measured.

Mice were anesthetized using Ketalar/Selactar 56 days after the initiation of immunization, exsanguinated via cardiopuncture, and euthanized. Immediately thereafter, nasal cavity lavages and bronchoalveolar lavages were sampled. Thereafter, the nasal cavity lavages and the bronchoalveolar lavages were stored on ice or refrigerated until ELISA assays were initiated.

ELISA assays were carried out in the manner described below. The split vaccine antigens were applied to a plate at concentration of 1 µg/ml (4° C., overnight), and blocking was carried out with 1% BSA/PBST (Tween 20: 0.5%) by allowing the plate to stand at room temperature for 2 hours. The serum sample was serially diluted using 1% BSA/PBST (Tween 20: 0.5%). As secondary antibody, HRP-labeled antibody in accordance with subclasses was used. After color had developed, OD was measured using a plate reader, and the amounts of influenza-antigen-specific antibody produced were measured. The nasal cavity lavages and the bronchoalveolar lavages were serially diluted using 1% BSA/PBST (Tween 20: 0.5%). In order to evaluate adjuvant effects of the BHA complex to potentiate the antigen-specific mucosal immunity, the amount of influenza-antigen-specific mucosal IgA produced was measured.

(3) Test Results

Figure 9:
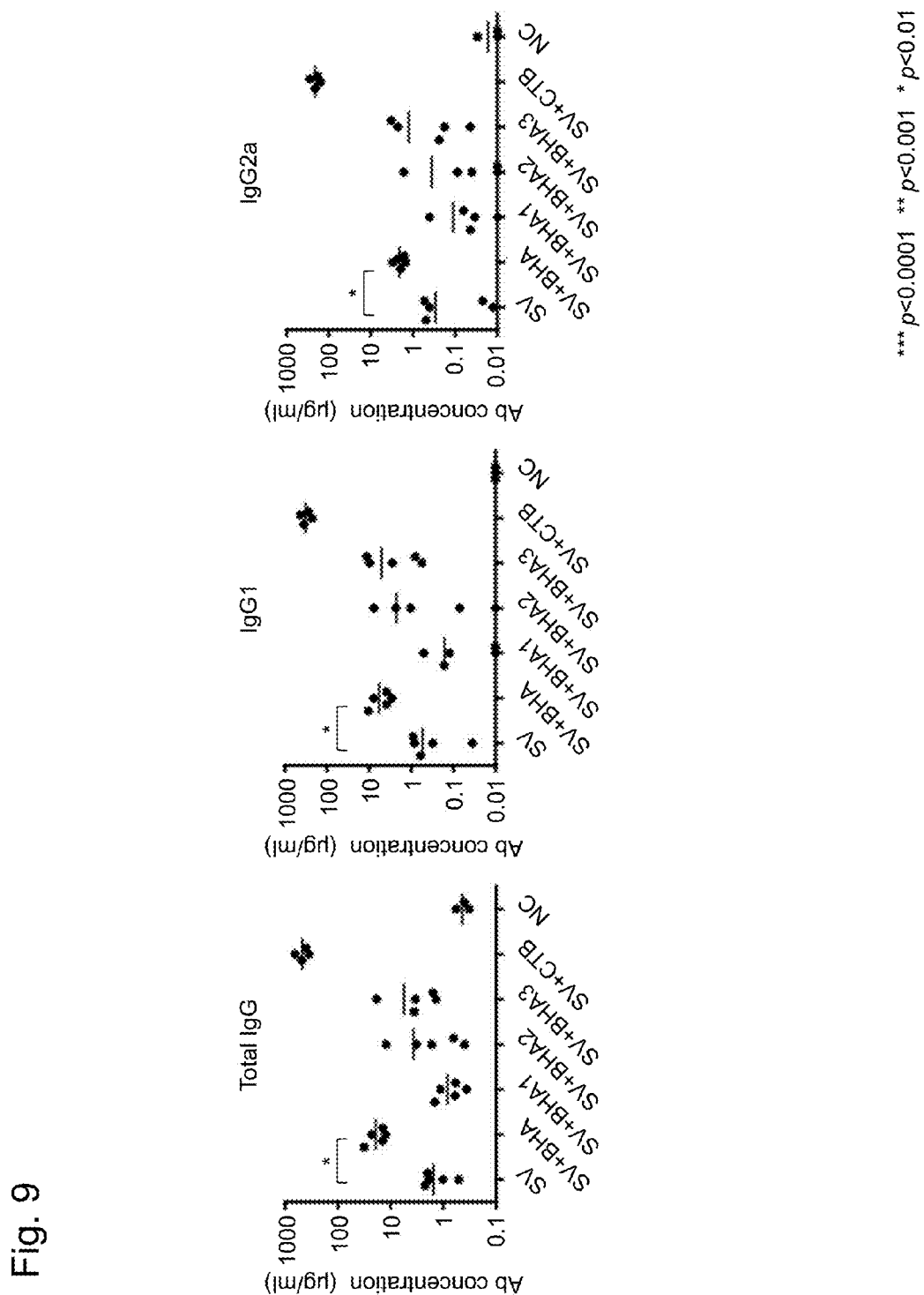
FIG. 9 shows the results of ELISA that measured the concentration of influenza-antigen-specific IgG in the sera (SV: the group to which influenza split vaccine alone is administered; SV+BHA: the group to which influenza split vaccine with BHA complex are administered; SV+BHA1-3: the group to which influenza split vaccine with BHA1, BHA2, or BHA3 are administered; SV+CTB: the group to which influenza split vaccine with *cholera* toxin B subunit are administered; NC: the group to which no antigens with adjuvants is administered (*$p<0.0001$ $p<0.001$ *$p<0.01$)).

FIG. 9 shows the results of measurement of the level of influenza-antigen-specific IgG in the sera (56 days after the initiation of immunization).

As shown in FIG. 9, the level of the antigen-specific antibody reactions in the sera induced in the group subjected to immunization with the BHA complex (BHA) adjuvant in combination with the influenza antigens was significantly higher than that induced in the group subjected to immunization with influenza antigens alone. Such phenomenon was observed in all the evaluated IgG subclasses. In the group subjected to immunization with the BHA1, BHA2, or BHA3 adjuvants that are composing elements of the complex in combination with the influenza antigens, in contrast, antibody reactions in the sera were not significantly potentiated, compared with the group subjected to immunization with the influenza antigens alone. When intradermal administration via injection was employed instead of intranasal administration, antibody reactions in the sera were not significant in any of the groups subjected to immunization with the BHA complex (BHA) adjuvant, the BHA1 adjuvant, the BHA2 adjuvant, or the BHA3 adjuvant in combination with the influenza antigens.

Figure 10:
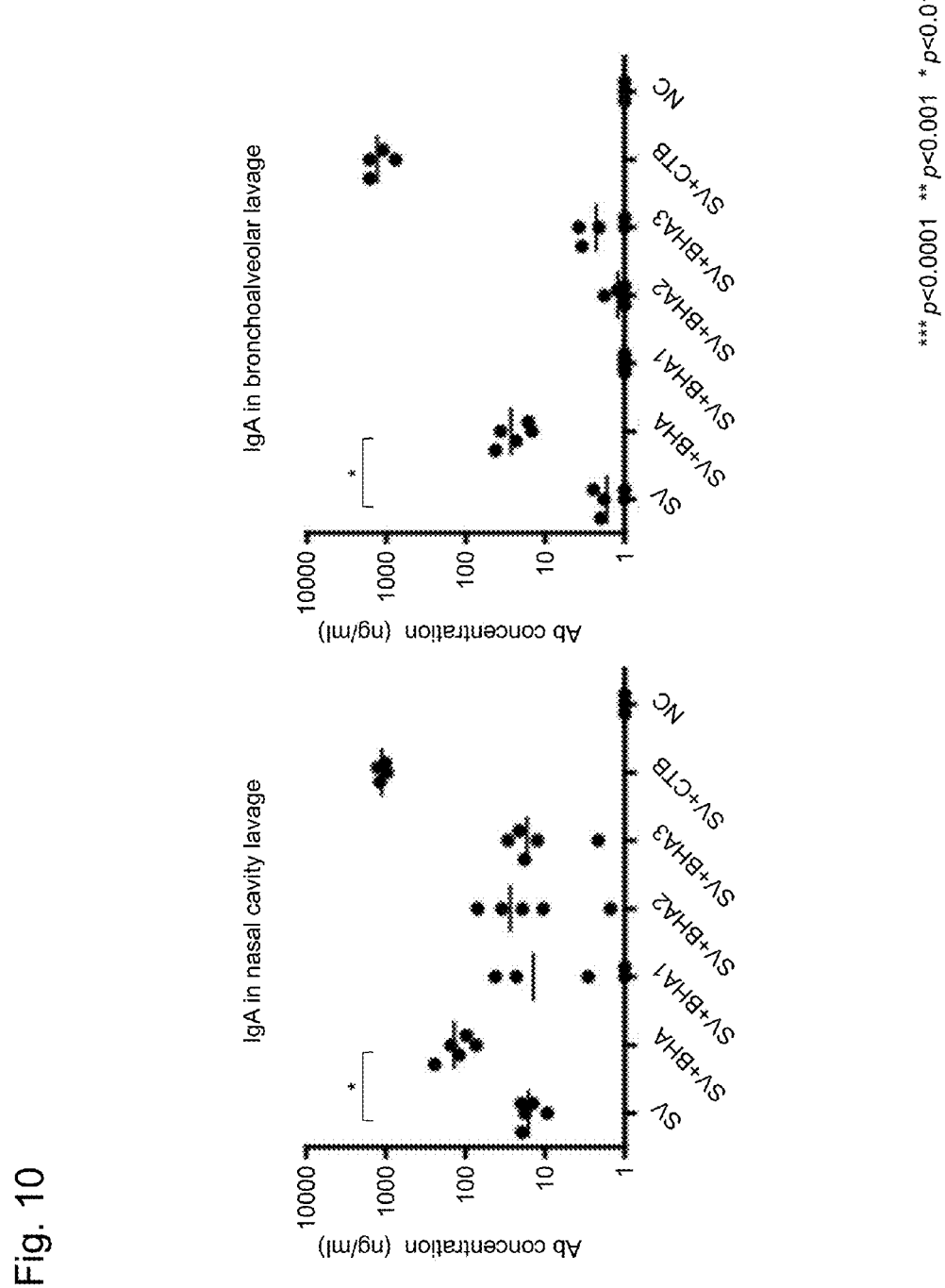
FIG. 10 shows the results of ELISA that measured the concentration of influenza-antigen-specific IgA in the nasal cavity lavage and in the bronchoalveolar lavage (SV: the group to which influenza split vaccine alone is administered; SV+BHA: the group to which influenza split vaccine with BHA complex are administered; SV+BHA1-3: the group to which influenza split vaccine with BHA1, BHA2, or BHA3 are administered; SV+CTB: the group to which influenza split vaccine with cholera toxin B subunit are administered; NC: the group to which no antigens with adjuvants is administered (*$p<0.0001$ $p<0.001$ *$p<0.01$)).

FIG. 10 shows the results of measurement of the amount of secretory IgA in the nasal cavity lavages and in the bronchoalveolar lavages. As shown in FIG. 10, the amount of antigen-specific IgA was significantly higher in the group subjected to immunization with the BHA complex (BHA) adjuvant in combination with the influenza antigens than in the group subjected to immunization with the influenza antigens alone. In contrast, the amount of secretory IgA was not significantly increased in the group subjected to immunization with the BHA1, BHA2, or BHA3 adjuvants that are composing elements of the BHA complex in combination with the influenza antigens, compared with the group subjected to immunization with the influenza antigens alone. When intradermal administration via injection was employed instead of intranasal administration, the amount of secretory IgA production was below the detection limit in all the groups subjected to immunization with the BHA complex (BHA) adjuvant, the BHA1 adjuvant, the BHA2 adjuvant, or the BHA3 adjuvant in combination with the influenza antigens.

INDUSTRIAL APPLICABILITY

The present invention is applicable in the field of production of a mucosal adjuvant and a mucosal vaccine preparation comprising such adjuvant.

All publications, patents, and patent applications cited herein are incorporated herein by reference in their entirety.

The invention claimed is:

1. A method of enhancing systemic and mucosal immune responses against a vaccine antigen in a subject, comprising administering to the subject an adjuvant comprising a protein complex composed of hemagglutinin (HA) subcomponents HA1, HA 2, and HA3 of *botulinum* toxin in combination with the vaccine antigen, wherein the protein complex is composed of (i) a protein consisting of the amino acid sequence as shown in SEQ ID NO : 1, (ii) a protein consisting of the amino acid sequence as shown in SEQ ID NO: 2 , and (iii) a protein consisting of the amino acid sequence as shown in SEQ ID NO : 3.

2. The method according to claim 1, wherein the adjuvant is administered to the subject simultaneously with the vaccine antigens, or before or after the vaccine antigens are administered.

3. The method according to claim 2, wherein the vaccine antigens are subunit antigens or inactivated antigens.

4. The method according to claim 2, where in the vaccine antigens are derived from pathogens causing mucosal infections.

5. The method according to claim 4, wherein the pathogens causing mucosal infections are viruses or bacteria.

6. The method according to claim 5, wherein the viruses are influenza viruses, human immunodeficiency viruses (HIV), chickenpox viruses, measles viruses, rubella viruses, mumps viruses, polioviruses, rotaviruses, adenoviruses, herpes viruses, RS viruses, dengue viruses, Japanese encephalitis viruses, severe acute respiratory syndrome (SARS) viruses, or hepatitis viruses.

7. The method according to claim 5, wherein the bacteria are *Bordetella pertussis, Neisseria meningitides*, type B influenza, pneumococcus, tuberculosis bacteria, tetanus bacilli, or *cholera bacilli*.

8. The method according to claim 1, wherein the adjuvant is administered with any mucosal routes.

9. The method according to claim 8, wherein the administration with mucosal routes is intranasal administration.

* * * * *